US011071866B2

(12) United States Patent
Casavant et al.

(10) Patent No.: US 11,071,866 B2
(45) Date of Patent: Jul. 27, 2021

(54) SYSTEMS AND METHODS FOR HIS-BUNDLE PACING

(71) Applicant: Cardiac Pacemakers, Inc., St. Paul, MN (US)

(72) Inventors: David Arthur Casavant, Reading, MA (US); David L. Perschbacher, Coon Rapids, MN (US); Ramesh Wariar, Blaine, MN (US); Stephen J. Hahn, Shoreview, MN (US); Allan Charles Shuros, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 246 days.

(21) Appl. No.: 16/174,816

(22) Filed: Oct. 30, 2018

(65) Prior Publication Data
US 2019/0126049 A1    May 2, 2019

Related U.S. Application Data

(60) Provisional application No. 62/580,711, filed on Nov. 2, 2017, provisional application No. 62/595,535, filed
(Continued)

(51) Int. Cl.
*A61N 1/36* (2006.01)
*A61N 1/368* (2006.01)
(Continued)

(52) U.S. Cl.
CPC ............ *A61N 1/368* (2013.01); *A61N 1/056* (2013.01); *A61N 1/362* (2013.01); *A61N 1/3684* (2013.01);
(Continued)

(58) Field of Classification Search
CPC .... A61N 1/368; A61N 1/056; A61N 1/36564; A61N 1/36922
See application file for complete search history.

(56) References Cited

U.S. PATENT DOCUMENTS

| 4,157,711 A | 6/1979 | Caspi et al. |
| 4,751,931 A | 6/1988 | Briller et al. |
| (Continued) | | |

FOREIGN PATENT DOCUMENTS

| CN | 111295224 A | 6/2020 |
| CN | 111295225 A | 6/2020 |
| (Continued) | | |

OTHER PUBLICATIONS

U.S. Appl. No 16/175,302, filed Oct. 30, 2018, "Systems and Methods for Recognizing His-Bundle Capture Type and Providing His-Bundle Pacing".

(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

Systems and methods for pacing cardiac conductive tissue are described. A medical system includes electrostimulation circuit that may generate His-bundle pacing (HBP) pulses for delivery at or near the His bundle. A capture verification circuit may detect, from a far-field signal representing ventricular response to the HBP pulses, a His-bundle response representative of excitation of the His bundle directly resulting from the HBP pulses, and a myocardial response representative of excitation of the myocardium directly resulting from the HBP pulses. A control circuit may adjust one or more stimulation parameters based on the His-bundle response and myocardial response. The electro- (Continued)

stimulation circuit may generate and deliver the HBP pulses according to the adjusted stimulation parameters to excite the His bundle.

20 Claims, 8 Drawing Sheets

Related U.S. Application Data on Dec. 6, 2017, provisional application No. 62/595,541, filed on Dec. 6, 2017.

(51) Int. Cl.
| | |
|---|---|
| *A61N 1/37* | (2006.01) |
| *A61N 1/05* | (2006.01) |
| *A61N 1/362* | (2006.01) |
| *A61N 1/365* | (2006.01) |
| *A61B 5/349* | (2021.01) |

(52) U.S. Cl.
CPC ..... *A61N 1/36507* (2013.01); *A61N 1/36521* (2013.01); *A61N 1/36564* (2013.01); *A61N 1/3712* (2013.01); *A61B 5/349* (2021.01); *A61N 1/36578* (2013.01); *A61N 1/371* (2013.01); *A61N 1/3702* (2013.01)

(56) References Cited

U.S. PATENT DOCUMENTS

| | | | |
|---|---|---|---|
| 5,174,286 | A | 12/1992 | Chirife |
| 5,800,467 | A | 9/1998 | Park et al. |
| 6,718,206 | B2 | 4/2004 | Casavant |
| RE43,569 | E | 8/2012 | Olson |
| 8,565,880 | B2 | 10/2013 | Dong et al. |
| 8,588,907 | B2 | 11/2013 | Arcot-Krishnamurthy et al. |
| 8,688,234 | B2 | 4/2014 | Ortega et al. |
| 8,761,880 | B2 | 6/2014 | Maskara et al. |
| 8,954,147 | B2 | 2/2015 | Arcot-Krishnamurthy et al. |
| 2002/0138014 | A1 | 9/2002 | Baura et al. |
| 2003/0120165 | A1 | 6/2003 | Björling |
| 2004/0049235 | A1 | 3/2004 | Deno et al. |
| 2007/0016261 | A1 | 1/2007 | Dong et al. |
| 2007/0239219 | A1* | 10/2007 | Salo .............. A61N 1/3627 607/18 |
| 2007/0273504 | A1 | 11/2007 | Tran |
| 2007/0276270 | A1 | 11/2007 | Tran |
| 2008/0001735 | A1 | 1/2008 | Tran |
| 2008/0004904 | A1 | 1/2008 | Tran |
| 2009/0005830 | A1 | 1/2009 | Zhu et al. |
| 2009/0054942 | A1 | 2/2009 | Zhu et al. |
| 2009/0227876 | A1 | 9/2009 | Tran |
| 2009/0259272 | A1 | 10/2009 | Reddy et al. |
| 2009/0318779 | A1 | 12/2009 | Tran |
| 2010/0256700 | A1 | 10/2010 | Shuros et al. |
| 2010/0262204 | A1 | 10/2010 | Mccabe et al. |
| 2011/0115624 | A1 | 5/2011 | Tran |
| 2011/0125041 | A1* | 5/2011 | Fischell .............. A61B 5/0456 600/515 |
| 2011/0181422 | A1 | 7/2011 | Tran |
| 2011/0245702 | A1 | 10/2011 | Clark et al. |
| 2011/0264158 | A1 | 10/2011 | Dong et al. |
| 2011/0319956 | A1* | 12/2011 | Zhu .............. A61N 1/36842 607/25 |
| 2012/0004564 | A1 | 1/2012 | Dobak, III |
| 2012/0092157 | A1 | 4/2012 | Tran |
| 2012/0095352 | A1 | 4/2012 | Tran |
| 2012/0157822 | A1 | 6/2012 | Van et al. |
| 2012/0239106 | A1 | 9/2012 | Maskara et al. |
| 2012/0283587 | A1 | 11/2012 | Gosh et al. |
| 2012/0284003 | A1 | 11/2012 | Gosh et al. |
| 2012/0330109 | A1 | 12/2012 | Tran |
| 2013/0009783 | A1 | 1/2013 | Tran |
| 2013/0158621 | A1 | 6/2013 | Ding et al. |
| 2013/0172691 | A1 | 7/2013 | Tran |
| 2013/0231574 | A1 | 9/2013 | Tran |
| 2013/0261685 | A1 | 10/2013 | Shuros et al. |
| 2014/0107724 | A1 | 4/2014 | Shuros et al. |
| 2014/0172035 | A1* | 6/2014 | Shuros .............. A61N 1/365 607/18 |
| 2016/0228709 | A1 | 8/2016 | Ternes et al. |
| 2018/0043071 | A1* | 2/2018 | Huibregtse .......... A61M 5/172 |
| 2019/0022378 | A1 | 1/2019 | Prillinger et al. |
| 2019/0126040 | A1 | 5/2019 | Shuros et al. |
| 2019/0126050 | A1 | 5/2019 | Shuros et al. |

FOREIGN PATENT DOCUMENTS

| | | |
|---|---|---|
| CN | 111405925 A | 7/2020 |
| WO | WO-2019089510 A1 | 5/2019 |
| WO | WO-2019089528 A1 | 5/2019 |
| WO | WO-2019089539 A1 | 5/2019 |

OTHER PUBLICATIONS

U.S. Appl. No 16/175,374, filed Oct. 30, 2018, "Systems and Methods for Correcting Cardiac Conduction Abnormality Using His-Bundle Pacing".

"U.S. Appl. No. 16/175,302, Non Final Office Action dated Aug. 27, 2020", 9 pgs.

"U.S. Appl. No. 16/175,302, Response filed Jun. 22, 2020 to Restriction Requirement dated May 5, 2020", 7 pgs.

"U.S. Appl. No. 16/175,302, Restriction Requirement dated May 5, 2020", 5 pgs.

"U.S. Appl. No. 16/175,374, Notice of Allowance dated Jul. 10, 2020", 12 pgs.

"U.S. Appl. No. 16/175,374, Response filed Jun. 22, 2020 to Restriction Requirement dated Apr. 23, 2020", 8 pgs.

"U.S. Appl. No. 16/175,374, Restriction Requirement dated Apr. 23, 2020", 8 pgs.

"International Application Serial No. PCT/US2018/058102, International Preliminary Report on Patentability dated May 14, 2020", 7 pgs.

"International Application Serial No. PCT/US2018/058102, International Search Report dated Dec. 12, 2018", 5 pgs.

"International Application Serial No. PCT/US2018/058102, Written Opinion dated Dec. 12, 2018", 5 pgs.

"International Application Serial No. PCT/US2018/058125, International Search Report dated Jan. 4, 2019", 4 pgs.

"International Application Serial No. PCT/US2018/058125, Written Opinion dated Jan. 4, 2019", 5 pgs.

"International Application Serial No. PCT/US2018/058140, International Preliminary Report on Patentability dated May 14, 2020", 8 pgs.

"International Application Serial No. PCT/US2018/058140, International Search Report dated Dec. 12, 2018", 5 pgs.

"International Application Serial No. PCT/US2018/058140, Written Opinion dated Dec. 12, 2018", 6 pgs.

Deshmukh, P., et al., "Permanent, Direct His-Bundle Pacing: A Novel Approach to Cardiac Pacing in Patients With Normal His-Purkinje Activation", Circulation, 101(8), (Feb. 29, 2000), 869-877.

Huang, Weijian, et al., "Feasibility of His Bundle Pacing to Correct Left Bundle Branch Block in Heart Failure Patients", Journal of the American College of Cardiology, vol. 70, No. 16, Suppl C, 2017, GW28-e1237,1 page.

Teng, Alexandra E., "Physiological mechanisms of QRS narrowing in bundle branch block patients undergoing permanent His bundle pacing", Journal of Electrocardiology 49 (2016) 644-648.

* cited by examiner

SYSTEMS AND METHODS FOR HIS-BUNDLE PACING

CLAIM OF PRIORITY

This application claims the benefit of priority under 35 U.S.C. § 119(e) of U.S. Provisional Patent Application Ser. No. 62/580,711, filed on Nov. 2, 2017, U.S. Provisional Patent Application Ser. No. 62/595,535, filed on Dec. 6, 2017, and U.S. Provisional Patent Application Ser. No. 62/595,541, filed on Dec. 6, 2017, each of which is herein incorporated by reference in its entirety.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further result in a decrease in cardiac output and deterioration of ventricular function. BiV pacing involves RV pacing via one lead, and LV pacing via another lead, and has been demonstrated to restore substantially simultaneous contraction of both ventricles. However, the potential adverse impact on ventricular function produced by the RV apex pacing may still exist in bi-ventricular pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall can be complex and challenging in some patients.

OVERVIEW

Hemodynamic response to artificial pacing can depend on many factors, including pacing site and the manner of which the pacing is performed. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional pacing because the propagation of the activation sequence can be much slower when it occurs through working myocardium versus activation through the intrinsic specialized conduction system of the heart. The cells of the specialized conduction system can propagate an activation signal about four times faster than working myocardium. A cardiac rhythm or functional management device configured to pace the His bundle is an alternative to conventional ventricular pacing. Pacing the His-bundle can activate the heart's natural conduction system, including the left and right bundle branches and Purkinje fibers, and produce efficient and coordinated cardiac response. The potentially long-term harmful hemodynamic effects that may occur from continuous RV apex pacing may also be reduced.

However, the artificial cardiac pacing system targeting the natural specialized cardiac conduction system, when not being used effectively, may result in dyssynchronous myocardial contraction. For example, stimulation near the His bundle may cause dyssynchronous patterns when the electrical stimulation fails to activate the His bundle, but only activates the para-Hisian myocardium surrounding the His bundle, an undesirable event referred to as para-Hisian capture. In some cases, the His-bundle pacing may activates both the His bundle and the adjacent working myocardium, an event referred to as non-selective His bundle capture. There is an unmet need for an artificial cardiac pacing system that can produce desirable therapeutic effects of coordinated ventricular contraction sequence via His bundle excitation, while reducing or eliminating unintended activation of non-targeted portions of the heart, such as the para-Hisian myocardium. Additionally, it is desired to retain the option of backup ventricular pacing should the His-bundle pacing fail to induce propagating action potentials, such as due to inadequate stimulation energy, His-bundle pacing lead failure, or a development of heart block inferior to the His bundle.

Embodiments of the present subject matter provide systems, devices, and methods for pacing a cardiac conductive tissue, such as a His bundle. One example of such a medical system includes circuitry for delivering a His-bundle pacing (HBP) pulse at or near a His bundle, and sensing far-field cardiac electrical signal representing ventricular contraction in response to the HBP pulse delivery. A capture verification circuit may detect a His-bundle response representative of excitation of the His bundle directly resulting from the delivery of the HBP pulses, and myocardial response representative of excitation of the para-Hisian myocardium directly resulting from the delivery of the HBP pulses. In various examples, the medical system may classify a tissue response as one of a plurality of capture types, such as a selective His bundle capture, a non-selective His bundle capture, a para-Hisian capture, or loss of capture. The system may adjust one or more stimulation parameters based on the His-bundle response, the myocardial response, or the classified capture types. HBP pulses may be delivered at or near the His bundle according to the adjusted stimulation parameters to excite the His bundle.

Example 1 is a system for pacing a heart. The system comprises an electrostimulation circuit configured to generate a His-bundle pacing (HBP) pulse for delivery at or near a His bundle of the heart, a sensing circuit configured to sense a far-field cardiac electrical signal representing a ventricular response to the delivery of HBP pulse at or near the His bundle, and a control circuit coupled to the sensing circuit and configured to control the delivery of the HBP pulse according to one or more pacing parameters. The control circuit may include a capture verification circuit configured to detect, from the sensed far-field cardiac electrical signal, a His-bundle response representative of excitation of the His bundle directly resulting from the delivery of the HBP pulse, and a myocardial response representative of excitation of a para-Hisian myocardial tissue of the heart directly resulting from the delivery of the HBP pulse.

In Example 2, the subject matter of Example 1 optionally includes the sensing circuit that may be electrically coupled to one or more electrodes disposed at or near the His bundle to sense the far-field cardiac electrical signal.

In Example 3, the subject matter of any one or more of Examples 1-2 optionally includes the sensing circuit that may be electrically coupled to one or more electrodes disposed in an atrium to sense the far-field cardiac electrical signal.

In Example 4, the subject matter of any one or more of Examples 1-3 optionally includes the control circuit that may further include a parameter adjuster circuit configured to adjust at least one of the one or more pacing parameters based on the detected His-bundle response and the detected myocardial response. The electrostimulation circuit, coupled to the parameter adjuster circuit, may be configured to generate the HBP pulse for delivery at or near the His bundle according to the adjusted at least one pacing parameter to excite the His bundle.

In Example 5, the subject matter of any one or more of Examples 1-4 optionally includes a timing circuit configured to time the delivery of the HBP pulse after an atrial-to-His bundle (AH) interval from an intrinsic atrial activation or an atrial pacing event.

In Example 6, the subject matter of any one or more of Examples 1-5 optionally includes the sensing circuit that may be configured to detect a far-field R wave from the far-field cardiac electrical signal. The capture verification circuit may be configured to detect the His-bundle response and the myocardial response based on a timing of the detected far-field R wave relative to the delivery of the HBP pulse.

In Example 7, the subject matter of Example 6 optionally includes the capture verification circuit that may be configured to detect the His-bundle response if the far-field R wave is detected within a capture detection window, and to detect the myocardial response if no far-field R wave is detected within the capture detection window.

In Example 8, the subject matter of Example 7 optionally includes the control circuit that may be configured to time a delivery of an atrial pacing pulse after a ventriculoatrial interval. The ventriculoatrial interval may begin at the detected far-field R wave within the capture detection window, or at the end of the capture detection window if no far-field R wave is detected within the capture detection window.

In Example 9, the subject matter of any one or more of Examples 1-8 optionally includes the sensing circuit that may be configured to detect a far-field R wave from the far-field cardiac electrical signal. The capture verification circuit may be configured to detect the His-bundle response and the myocardial response based on a morphological feature of the detected far-field R wave.

In Example 10, the subject matter of Example 9 optionally includes the morphological feature that may include a width of the detected far-field R wave. The capture verification circuit may be configured to detect the His-bundle response if the width of the far-field R wave falls below a width threshold, and to detect the myocardial response if the width of the far-field R wave exceeds the width threshold.

In Example 11, the subject matter of any one or more of Examples 7-10 optionally includes the electrostimulation circuit that may be configured to deliver backup pacing at an end of the capture detection window if the capture verification circuit fails to detect the His-bundle response directly resulting from the delivery of the HBP pulse.

In Example 12, the subject matter of Example 11 optionally includes the backup pacing that may include a high-output pacing.

In Example 13, the subject matter of any one or more of Examples 11-12 optionally includes the electrostimulation circuit electrically coupled to one or more electrodes disposed at or near the His bundle or in the ventricle to deliver the backup pacing.

In Example 14, the subject matter of any one or more of Examples 1-13 optionally includes the control circuit that may be configured to determine a pacing threshold representing minimal energy to directly excite the His bundle. The electrostimulation circuit may be configured to deliver HBP pulses at or near the His bundle according to a pacing parameter programmed to a plurality of values. The sensing circuit may be configured to sense respective far-field R waves in response to the delivery of HBP pulses; and the control circuit is configured to determine the pacing threshold based on a step change in time intervals between the delivery of HBP pulses and the sensed respective far-field R waves.

In Example 15, the subject matter of Example 14 optionally includes the electrostimulation circuit that may be configured to deliver a series of HBP pulses with decreasing pacing amplitude. The control circuit may be configured to determine the pacing threshold to be a pacing amplitude corresponding to a step increase in the measured time intervals between the delivery of HBP pulses and the respective far-field R waves.

Example 16 is a method for operating a pacing system to stimulate a heart. The method comprises steps of generating a His-bundle pacing (HBP) pulse using an electrostimulation circuit and delivering the HBP pulse at or near the His bundle; sensing a far-field cardiac electrical signal using a sensing circuit, the far-field cardiac electrical signal representing a ventricular response to the delivery of the HBP pulse at or near the His bundle; and detecting a His-bundle response and a myocardial response from the sensed far-field cardiac electrical signal using a capture verification circuit, the His-bundle response representative of excitation of the His bundle directly resulting from the delivery of the HBP pulse, and the myocardial response representative of excitation of the myocardial tissue directly resulting from the delivery of the HBP pulse.

In Example 17, the subject matter of Example 16 optionally includes adjusting one or more pacing parameters using a parameter adjuster circuit in response to no detection of the His-bundle response directly resulting from the delivery of the HBP pulse.

In Example 18, the subject matter of Example 16 optionally includes delivering the HBP pulse includes timing the delivery of the HBP pulse after an atrial-to-His bundle (AH) interval from an intrinsic atrial activation or an atrial pacing event.

In Example 19, the subject matter of Example 16 optionally includes detecting a far-field R wave from the sensed far-field cardiac electrical signal, and detecting the His-bundle response and the myocardial response based on a timing of the detected far-field R wave relative to the delivery of the HBP pulse.

In Example 20, the subject matter of Example 19 optionally includes detecting the His-bundle response if the far-field R wave is detected within a capture detection window, and detecting the myocardial response if no far-field R wave is detected within the capture detection window.

In Example 21, the subject matter of Example 20 optionally includes delivering backup pacing at an end of the capture detection window if no His-bundle response is detected with the capture detection window.

In Example 22, the subject matter of Example 16 optionally includes detecting a far-field R wave from the sensed far-field cardiac electrical signal, and detecting the His-bundle response and the myocardial response based on a width of the detected far-field R wave of the detected far-field wave.

In Example 23, the subject matter of Example 16 optionally includes determining a pacing threshold representing minimal energy to directly excite the His bundle. The determination of the pacing threshold may include steps of: delivering a series of HBP pulses with decreasing pacing amplitude at or near the His bundle over multiple cardiac cycles; sensing, from each of the multiple cardiac cycles, a respective far-field R wave in response to the delivery of HBP pulse; and determining the pacing threshold based on a step increase in time intervals between the delivery of HBP pulses and the respective far-field R waves.

The systems, devices, and methods discussed in this document may improve the technology of cardiac pacing in patients with cardiac disease, such as heart failure. A technological challenge in cardiac pacing is improving patient cardiac performance without structural and functional changes that impair cardiac synchrony, such as due to long-term RV apex pacing. Particularly, in His-bundle pacing, timing for the delivery of the HBP pulses can be critical to ensure His-bundle capture and stimulation through the natural conduction pathways. Direct sensing of His potential for assessing capture status can be practically difficult and unreliable, at least because the His potential can be too week a signal to sense (e.g., typically less than one millivolt). Moreover, His potential typically does not precede a ventricular ectopic beat, such as a premature ventricular contraction (PVC); therefore, it may not be adequately used for timing the HBP pulse delivery in the presence of multiple PVCs. The present subject matter provides a technical solution to this challenge by using a far-field cardiac signal representative of ventricular response to the HBP pulses. The far-field cardiac signal may be sensed using one or more electrodes disposed at or near the His bundle, in an atrium, in the ventricle or associated veins in a ventricle. The far-field cardiac signal can be a stronger signal than local His potential, and therefore can be more reliably detected. Additionally, PVCs may be reliably sensed from the far-field cardiac signal. Because the far-field sensed PVCs (such as sensed at or near the His bundle) are typically not preceded by a His potential or His pacing pulse, they can be used to reset a ventriculoatrial interval for sensing an intrinsic atrial activation or for timing the delivery of atrial pacing in the next cardiac cycle. As such, the systems, devices, and methods discussed in this document improves cardiac pacing technology, particularly His-bundle pacing technology, with little to no additional cost or system complexity, at least because the physiological signals or composite metric measurements are also used for producing HF diagnostics. The His-bundle pacing as discussed in the present document may improve pacing efficiency utilizing the natural conduction mechanisms of the heart, while reducing long-term harmful hemodynamic effects associated with RV apex pacing. With improved synchrony and cardiac performance, fewer unnecessary medical interventions, such as drugs, procedures, or device therapies, may be scheduled, prescribed, or provided to such patients. As a result, overall system cost savings may be realized.

The His-bundle pacing guided by far-field cardiac signal as discussed in this document may also improve the functionality of a cardiac pacing system or device. As discussed above, the far-field cardiac signal representative of ventricular response to HBP pulses are stronger than local His potential. Compared to direct sensing of the His potential, simpler and less sophisticated processing is required to accurately and reliably detect far-field ventricular response. Memory usage may be more efficient by storing the His-bundle response, the myocardial response, or the classified capture types, which are clinically more relevant to pacing therapy efficacy. The therapy adjustment based on the classified capture types may not only improve therapy efficacy and patient outcome, but may also reduce unnecessary device therapies, extend battery life and implantable device longevity, or enable reduction of device size to achieve existing performance metrics.

While His-bundle pacing is specifically discussed in this document, this is meant only by way of example and not limitation. It is within the contemplation of the inventors, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for pacing cardiac conductive tissue. An embodiment of the system may include an electrostimulator to generate His-bundle pacing (HBP) pulses for delivery at or near the His bundle. The system may sense a far-field signal representing ventricular response to the HBP pulses, and detects a His-bundle response and a myocardial response from at least the far-field signal. The system may classify a tissue response to HBP into one of a plurality of capture types. In an example, classification of tissue response may be based on the sensed near-field cardiac activity and the sensed far-field cardiac activity. The system may adjust one or more stimulation parameters based on the His-bundle response and myocardial response, or the classified capture types, and deliver HBP pulses according to the adjusted stimulation parameters to excite the His bundle.

Figure 1:
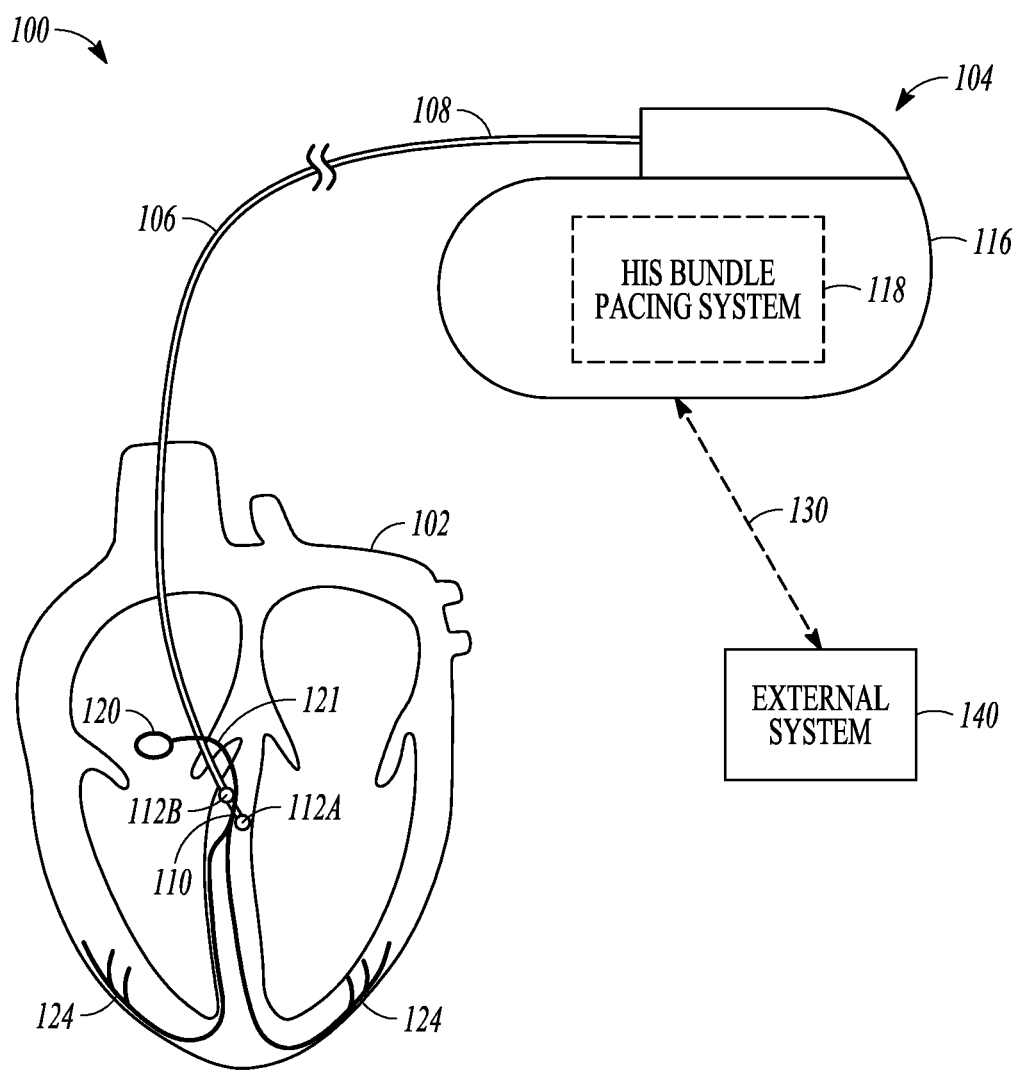
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-B, are positioned in or on a His bundle 121, a region distal to the blocked or slowly conducting AV node and in the AV septum, an interventricular septum region, or a right atrial region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-B, are positioned at or near other parts of the natural conduction pathways, such as one of the bundle branches 122 or 123, the Purkinje fibers 124, or other conductive tissues, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In various examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses for delivery at or near the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or bipolar His-bundle pacing may be selected by a system user from a plurality of candidate electrodes from one or more leads of the lead system, and programmed into the His-bundle pacing system 118.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others.

The His-bundle pacing system 118 may sense a cardiac electrical or mechanical signal in response to the delivery of HBP pulses using one or more electrodes or physiologic sensors. In an example, the His-bundle pacing system 118 may sense a far-field cardiac electrical signal representative of ventricular contractions using electrodes disposed at or near the His bundle (e.g., one or more of the electrodes 112A and 112B), or electrodes disposed in an atrium. The His-bundle pacing system 118 may verify His bundle capture using the sensed far-field cardiac electrical signal. In an example, the His-bundle pacing system 118 may detect a His-bundle response representative of excitation of the His bundle directly resulting from the delivery of HBP pulses, and a detection of myocardial response representative of excitation of the para-Hisian myocardium directly resulting from the delivery of HBP pulses. In another example, the His-bundle pacing system 118 may classify a tissue response into one of a plurality of capture types. The His-bundle pacing system 118 may determine whether the HBP pulses need to be adjusted to better capture the His bundle, based on the His-bundle response, the myocardial response, or the classified capture types. For example, if only the myocardial response is detected without a detection of His-bundle response, then the His-bundle pacing system 118 may adjust one or more stimulation parameters such that the HBP pulses delivered in accordance with the adjusted stimulation parameters may directly excite the His bundle. If neither myocardial response nor the His-bundle response is detected, which indicates no tissue capture resulted from the HBP pulses, then the His-bundle pacing system 118 may deliver backup ventricular pacing to improve myocardial contractility.

The IMD 104 may be configured to communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, or classify tissue response to one of a plurality of capture types. The capture verification or classification may be carried out periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the DAD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
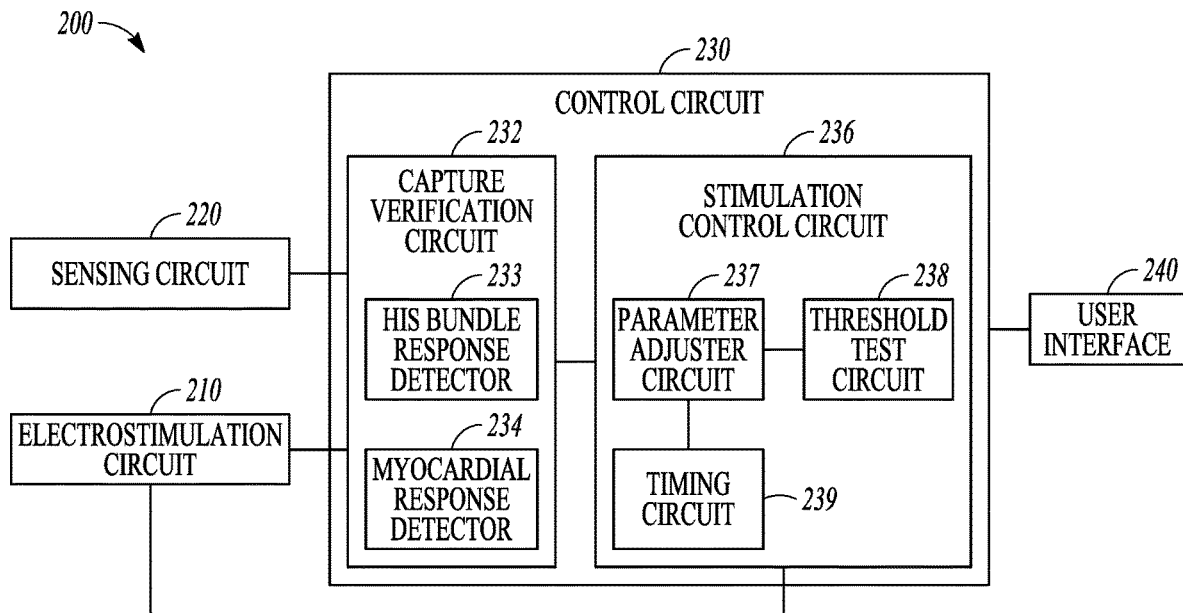
FIG. 2 is a block diagram illustrating an example of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, a control circuit 230, and a user interface 240.

The electrostimulation circuit 210 may be configured to generate stimulation energy for delivery to the heart 102 via one or more leads and the associated electrodes. The electrostimulation circuit 210 may be configured to generate His-bundle pacing (HBP) pulses for delivery to a target site at or near the His bundle such as via the lead 106 and one or more of the electrodes 112A-B. The target site may include an interventricular septum region or a right atrial region near the His-bundle, or other conductive tissues such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation for delivery at non-cardiac tissues such as nerve tissues, muscle tissues, or other excitable tissues.

The electrostimulation circuit 210 may generate the HBP pulses according to programmed stimulation parameters, such as provided by control circuit 230. Examples of the stimulation parameters may include information about stimulation site, stimulation strength, stimulation mode, or stimulation timing, among other parameters. The stimulation site includes information about pacing site, pacing vector configuration (e.g., anode and cathode electrodes), or unipolar or bipolar pacing. The stimulation site may additionally include cardiac resynchronization therapy (CRT), which include (BiV) pacing of both left and right ventricles, or synchronized left ventricle (LV)-only pacing; single site pacing of only one site of a heart chamber (e.g., the left ventricle) within a cardiac cycle; or multisite pacing (MSP) of two or more sites of a heart chamber within the same cardiac cycle. The stimulation strength parameters determine the amount of energy delivered to the pacing site, and may include pulse amplitude, pulse width, pulse frequency, pulse waveform, duty cycle, or stimulation duration.

The stimulation mode may include an atrial-Hisian (AH) pacing mode, a His-ventricular (HV) pacing mode, or an atrial-His-ventricular (AHV) pacing mode. In the AH pacing mode, the HBP pulses may be delivered only when intrinsic atrial activation (As), or atrial pacing (Ap), fails to produce propagatable depolarization of the AV node and the His bundle. Compared to asynchronous mode where the HBP pulses are delivered at a fixed rate regardless of the His bundle response to the As or the Ap event, the demand AH pacing may eliminate the possibility for fusion beats when the excitation wave caused by the As or the Ap event and the local HBP excitation wave occur at the same time and collide with each other, which may reduce the pacing efficacy and lead to ventricular asystole and poor cardiac performance. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. Delivery of the ventricular pacing pulses or a detection of PVC may trigger a ventriculoatrial interval for sensing an intrinsic atrial activation or for timing the delivery of atrial pacing in the next cardiac cycle. The AHV pacing mode involves sequential atrial, Hisian, and ventricular pacing. One or more of the His-bundle pacing or the ventricular pacing may be delivered in a demand mode.

Patients with different medical conditions may be indicated for one of the His pacing modes. For example, the AH pacing mode may be used to treat patients with varying degrees of heart block or sick sinus syndrome. The HV pacing mode may be indicated for patients with persistent or chronic atrial fibrillation, or patients treated with atrioventricular node ablation to slow and regularize ventricular rhythm. The AHV pacing mode may be indicated for patients with cardiac dyssynchrony and having received cardiac resynchronization therapy, patients suffering from heart failure with left bundle branch block, heart failure induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an As or an Ap event. An AH timing represents a latency period, within a cardiac cycle, from an intrinsic As event or an Ap event to the delivery of a HBP pulse. In demand HV pacing mode, the ventricular pacing pulses are timed relative to a His pacing event. An HV timing represents a latency period, within a cardiac cycle, from a His bundle event (e.g., a HBP pulse) to the delivery of ventricular pacing pulse. In an example, if an HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an As or Ap event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP as discussed in this document, the "selective His-bundle pacing" refers to delivering HBP pulses, at or near a His bundle region, which causes only the excitation (depolarization) of the His bundle, without substantial unintended and undesirable excitation of the muscle tissue adjacent to the His bundle (also known as the para-Hisian myocardium) directly caused by the pacing pulses. The "non-selective His-bundle pacing" refers to delivering HBP pulses that causes the both the excitation (depolarization) of the His bundle, and unintended excitation of para-Hisian myocardium directly caused by the pacing pulses. In some examples, the HBP is a "para-Hisian pacing", when the delivery of the HBP pulses causes only excitation of the para-Hisian myocardium or other un-intended cardiac tissues, without substantial intended excitation of the His bundle directly caused by the pacing pulses.

The sensing circuit 220 may be coupled to one or more electrodes or physiologic sensors to sense a signal indicative of a response of a portion of the heart 102 to the delivery of HBP pulses. Examples of the sensed signals may include: an electrocardiogram (ECG); an electrogram (EGM) of a portion of the heart such as atrial EGM, ventricular EGM, or evoked His potential; an impedance signal; a heart sound signal; or a pressure signal, among other physiological or hemodynamic signals indicative of a tissue response to the delivery of HBP pulses.

In various examples, the sensing circuit 220 may be configured to sense a far-field cardiac electrical signal representing ventricular response to the delivery of the HBP pulses. In an example, the far-field cardiac electrical signal may be sensed using a unipolar sense vector comprising an electrode disposed at or near the His bundle or in an atrium, and a reference electrode distal to the His bundle, such as the housing 116 of the IMD 104. In another example, the far-field cardiac electrical signal may be sensed using a bipolar sense vector comprising two electrodes disposed at or near the His bundle or in an atrium. The electrode(s) for sensing the far-field cardiac electrical signal may be the same electrodes used for delivering HBP pulses. Alternatively, different electrodes may be used for sensing the far-field cardiac electrical signal.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, the far-field ventricular response to the HBP pulses. In an example, the first and second devices are both implantable devices. In another example, at least one of the first or the second device is a non-implantable, wearable device.

Unlike the near-field signal sensed directly from an electrode disposed in the ventricle, the far-field cardiac electrical signal may not require electrodes in direct contact with the ventricle. As such, it may be particularly suitable for patients indicated for AH pacing mode without an implantation of a dedicated ventricular lead. Far-field signals may also provide a global perspective to the activation of the heart. For example, both atrial and ventricular activity may be present on a far-filed signal. Furthermore, the far-field signal characteristics such as the morphology may provide information about the type of activation, for example normal ventricular activation vs. a PVC. The sensed far-field cardiac electrical signal may be used by the control circuit 230 to verify His bundle capture, or to classify a tissue response into one of a plurality of capture types. Examples of far-field ventricular response to HBP and the capture verification based on the far-field ventricular response are discussed below, such as with reference to FIG. 4.

The control circuit 230 may be configured to verify that the HBP pulses capture one or more of the conductive tissues, such as the His bundle or the myocardium, and to control the delivery of the pacing pulses based on the capture status. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a capture verification circuit 232 and a stimulation control circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 may be coupled to the electrostimulation circuit 210 and the sensing circuit 220, and configured to verify His bundle capture by detecting a His-bundle response and a myocardial response from the sensed far-field cardiac electrical signal. The capture verification circuit 232 may perform capture verification according to a specified schedule, such as on a periodic basis, or continuously on a beat-by-beat basis (i.e., verifying capture in response to each HBP pulse). The capture verification circuit 232 may include a His-bundle response detector 233 configured to detect the His-bundle response, and a myocardial response detector 234 configured to detect the myocardial response. The His-bundle response is representative of His bundle capture, which is excitation of the His bundle directly resulting from the delivery of the HBP pulse. The myocardial response is representative of myocardial capture, which is excitation of the myocardium directly resulting from the delivery of the HBP pulse. In an example, HBP pulses are delivered in multiple cardiac cycles, such that at least one pulse is delivered in each of the multiple cardiac cycles. The His bundle response detector 233 and the myocardial response detector 234 may respectively detect a His-bundle response and a respective myocardial response for each of the multiple cardiac cycles using the sensed far-field cardiac electrical signal.

In some examples, the detection of the His-bundle response and the myocardial response may be based on a timing of a far-field ventricular event in response to the delivery of HBP pulses. A bipolar far-field cardiac electrical signal may be sensed using two electrodes disposed at or near the His bundle or in an atrium. Such a bi-polar far-field cardiac electrical signal may provide accurate timing of far-field ventricular response. In an example, the capture verification circuit 232 may measure a time interval (HV interval) between a HBP pulse and an evoked far-field ventricular activity, such as a far-field R (FFR) wave, sensed from the far-field cardiac electrical signal. Generally, a His-bundle response may be characterized by a short HV interval due to faster propagation of the His bundle depolarization through the natural conduction pathway (e.g., His bundle, bundle branches, and Purkinje fibers). In contrast, a myocardial response may be characterized by a relatively longer HV interval due to relatively slower, cell-to-cell conduction of the depolarization.

In an example, the His bundle response detector 233 and the myocardial response detector 234 may be configured to detect respectively a His-bundle response and a myocardial response using a capture detection window ($W_D$). The capture detection window may begin at the delivery of each of the HBP pulses, and have a specified window duration ($L_W$). If far-field ventricular depolarization is detected within the window $W_D$, then a His-bundle response is deemed detected. If no far-field ventricular depolarization is detected within the window $W_D$, then a myocardial response is deemed detected. The window duration $L_W$ may be programmed to a value that can distinguish the slower myocardial response from the faster His-bundle response. In an example, $L_W$ is approximately 50-120 milliseconds (msec). In some examples, $L_W$ may be at least partially automatically determined and dynamically updated based on patient historical HBP capture data, such that $L_W$ is longer than the HV intervals corresponding to the historical His-bundle responses, and shorter than the HV intervals corresponding to the historical myocardial responses.

In some examples, the detection of the His-bundle response and the myocardial response may be based on a morphology of the far-field ventricular activity, such as a FFR wave. A unipolar far-field cardiac electrical signal may be sensed using an electrode disposed at or near the His bundle or in an atrium, and a reference electrode such as the housing 116 of the IMD 104. In some examples, an array of electrodes on the housing 116 may be electrically connected to increase the area of electrode-tissue interface. Morphology of a unipolar far-field cardiac electrical signal may be more reliably enable classification of different types of ventricular responses. Due to the different conduction pathways involved and different conduction properties (e.g., velocity), the His-bundle response and the myocardial response may demonstrate different ventricular EGM morphologies, which can be detected from the far-field cardiac electrical signal. For example, a His-bundle response (representative of His capture) may be characterized by a narrower far-field QRS complex or FFR wave due to fast conduction and more coordinated contraction of the ventricles. A myocardial response (representative of myocardial capture) may be characterized by a wider far-field QRS complex or FFR wave due to relatively slower, cell-to-cell conduction, and less coordinated contraction of the ventricles.

The capture verification circuit 232 may extract from the sensed far-field ventricular depolarization one or more morphological features, such as an R wave width, a slope of the upstroke or down-stroke branch of the R wave, or an area under the curve of the FFR wave, among others. The His bundle response detector 233 and the myocardial response detector 234 may be configured to detect respectively a His-bundle response and a myocardial response, corresponding to each delivered HBP pulse, using the extracted one or more morphological features. In an example, the FFR wave may be detected using an R wave amplitude threshold. The width of FFR wave may be measured as an interval between the crossings of the R wave amplitude threshold in the upstroke and the down-stroke of the FFR wave. The His-bundle response detector 233 may detect the His-bundle response if the measured width the FFR wave falls below a width threshold. The myocardial response detector 234 may detect a myocardial response if the measured widths of the FFR wave exceeds the width threshold. The width threshold may be programmed to a value such as to better distinguish slower, cell-to-cell myocardial response from faster His-bundle response. In an example, the width threshold is approximately 90-120 msec. In another example, the width threshold is approximately 120-140 msec. In an example, the width threshold may be at least partially automatically determined and dynamically updated based on patient historical HBP capture data, such as FFR wave width for myocardial response and the FFR wave width for His-bundle response.

In some examples, the detection of the His-bundle response and the myocardial response may be based on a near-field para-Hisian myocardial EGM and a far-field cardiac EGM. The near-field para-Hisian myocardial EGM may be sensed within a first time window using a bipolar sense vector comprising two electrodes at or near the His bundle (e.g., electrodes 112A and 112B). The far-field cardiac EGM may be sensed within a second time window using a unipolar sense vector comprising an electrode at or near the His bundle (e.g., one of the electrode 112A or 112B) and a reference electrode distal to the His bundle (e.g., housing 116, or one or more electrodes on the housing 116). Examples of the near-field para-Hisian myocardial EGM and the far-field cardiac EGM for detecting the His-bundle response and the myocardial response are discussed below, such as with reference to FIGS. 3 and 4.

The stimulation control circuit 236 may include one or more of a parameter adjuster circuit 237, a threshold test circuit 238, and a timing circuit 239. The parameter adjuster circuit 237 may be configured to adjust at least one of the stimulation parameters according to the detected His-bundle response and the detected myocardial response. The parameter adjustment may be performed periodically at specified time period, or triggered by a specific event. The parameter adjustment may be automatically executed, or programmed by a user (e.g., a clinician) via a user interface 240. In an example, the capture verification circuit 232 may classify the His capture status into one or more capture types based on the detections of the His-bundle response and the myocardial response. Examples of the capture types may include selective His bundle capture, non-selective His bundle capture, or para-Hisian capture, as to be discussed with reference to FIG. 3.

The parameter adjuster circuit 237 may adjust one or more of the stimulation parameters for HBP based on the His-bundle response, the myocardial response, or the classified capture types, such that the HBP may more effectively activate patient natural conduction system to stimulate the heart and to improve cardiac performance, in an example, the parameter adjuster circuit 237 may adjust stimulation site, such as by switching to a different stimulation vector configuration including an electrode in close proximity to the His bundle to improve the likelihood of selectively capturing the His-bundle. In another example, the parameter adjuster circuit 237 may adjust stimulation timing, such as the AH timing relative to an intrinsic or paced atrial event. In an example, the parameter adjuster circuit 237 may adjust stimulation strength, such as one or more of pulse amplitude, pulse width, pulse frequency, pulse waveform, duty cycle, or stimulation duration. In an example, the parameter adjuster circuit 237 may adjust stimulation mode, such as switching from AH mode to HV mode when a patient develops persistent or chronic atrial fibrillation, or treated with atrioventricular node ablation. In another example, the parameter adjuster circuit 237 may switch from AH pacing mode to AHV mode in response to a change in patient condition, such as a development of bundle branch block. AHV mode may also be used in patients with an AH indication, such as to provide backup ventricular pacing via a ventricular lead in case that HBP pulses do not always induce ventricular depolarization. Additionally, the AHV mode may be used in CRT patients who already have an RV lead implanted for cardiac pacing and optionally defibrillation therapy. In an example, the parameter adjustment may be continued until the His-bundle response is detected, which indicates that HBP pulses elicit propagatable excitation of the His bundle. In another example, the parameter adjustment may be continued until only the His-bundle response, but no myocardial response, is detected, which indicates that HBP pulses elicit only propagatable excitation of the His bundle without excitation of the para-Hisian myocardium.

Improper assessment of HB threshold can result in para-Hisian capture and ventricular dyssynchrony. Para-Hisian capture refers to excitation of only the para-Hisian muscle without excitation of the His bundle directly caused by the delivery of HBP pulses. The pacing threshold test circuit 238 may be configured to determine a pacing threshold representing minimal energy required to excite the His bundle. In various examples, the parameter adjuster circuit 237 may adjust one or more stimulation parameters using the determined pacing threshold. The pacing threshold may be determined during implant of the IMD 104, periodically at specified time period, or triggered by a specific event, such as the HBP pulses failing to excite the His bundle, or a user command. The threshold test may include delivering HBP pulses (e.g., via the electrostimulation circuit 210) at or near the His bundle in accordance with a threshold test protocol. The threshold test protocol defines varying a stimulation parameter at a specified manner, such as ramping up or ramping down the pulse amplitude. The capture verification circuit 232 may measure time intervals (HV interval) between the delivery of HBP pulses with varying pulse amplitude and the corresponding sensed far-field ventricular responses, such as far-field R (FFR) waves. The FFR waves may be detected in a capture detection window ($W_D$) that begins at the delivery of HBP pulse and has a window duration of L. To ensure proper detection of FFR waves, the window duration L may be initialized to approximately 150 msec. A central tendency measure of the HV intervals ($HV_C$), such as an average or a median of the HV intervals over a plurality of cardiac cycles (e.g., 5-10 cardiac cycles), may be determined. The window duration L may then be updated to be greater than the $HV_C$ by a specified margin $\delta$, that is, $L=HV_C+\delta$. Alternatively, the detection window ($W_D$) may be defined as a neighborhood of the $HV_C$. In an example, $W_D$ begins at $HV_C-15$ msec, and ends at $HV_C+15$ msec.

The threshold test circuit 238 may be coupled to the capture verification circuit 232 to detect a step change in the measured HV interval in response to the delivery of the HBP pulses with varying pulse amplitude. For example, a step increase in HV interval indicates a transition from a propagatable His-bundle excitation to a para-Hisian myocardium only excitation without His-bundle capture. The threshold test circuit 238 may determine the pacing threshold to be the pulse amplitude corresponding to the detected step change in the measured HV interval. In an example, the pulse amplitude is decremented on every 3-5 beats, until the threshold test circuit 238 detects a step increase in the measured HV interval by at least 30 msec. The threshold test circuit 238 may determine the pacing threshold to be the highest pulse amplitude that results in the detected step increase in the measured HV interval. The parameter adjuster circuit 237 may adjust the stimulation strength, such as the His-bundle pacing amplitude, based on the pacing threshold. In an example, the His-bundle pacing amplitude may be adjusted to be 3-5 times the pacing threshold for an improved performance of His-bundle capture.

In some examples, the pacing threshold test circuit 238 may determine the pacing threshold using the morphology of the far-field ventricular response, such as FFR wave. The threshold test circuit 238 may monitor the FFR wave and detect a change in FFR wave morphology in response to the delivery of the HBP pulses with varying pulse amplitude. The change in FFR, wave morphology, such as a change in FFR wave width, indicates a transition from a propagatable His-bundle excitation to a para-Hisian myocardium only excitation without His-bundle capture. The threshold test circuit 238 may determine the pacing threshold to be the pulse amplitude corresponding to the detected change in FFR wave morphology.

The capture verification circuit may additionally use mechanical or hemodynamic sensors to determine the capture status, including detecting the His bundle response and myocardial response, or classifying a tissue response into one of capture types. Zhu et al. U.S. Pat. No. 8,688,234, entitled "DEVICES, METHODS, AND SYSTEMS INCLUDING CARDIAC PACING," refers to determining the effectiveness or completeness of His-bundle capture using attributes of a QRS signal, such as QRS narrowing, or using mechanical or hemodynamic sensors, which is incorporated herein by reference in its entirety. Dong et al. U.S. Pat. No. 8,565,880 entitled "HIS-BUNDLE CAPTURE VERIFICATION AND MONITORING," refers to His-bundle capture verification using hemodynamic sensors such as heart sound or blood pressure sensors, which is incorporated by reference herein in its entirety.

The timing circuit 239 may be configured to time the delivery of the HBP pulses according to a stimulation timing parameter, such as an adjusted stimulation timing provided by the parameter adjuster circuit 237 or programmed by a user via a user interface 240. In an example, the His-bundle pacing system 200 may be configured to operate in a demand AH pacing mode, and the timing circuit 239 may time the delivery of a HBP pulse using an atrial-to-His bundle (AH) timing. The AH timing is a programmable latency period with respect to an intrinsic (As) or paced atrial event (Ap). In an example, the AH timing may be programmed to approximately 50 msec shorter than a sensed P wave-to-R wave (PR) interval or a programmed atrial-to-ventricular (AV) delay within a cardiac cycle. In an example, a system user may program an AV delay and an HV interval, such that that AFT timing may be determined as AH=AV−HV. The HV interval may be programmed to approximately 50-80 msec, which determines how far in advance to the end of the AV delay that the HBP pulse is delivered. The AV delay may be a sensed AV delay between an As event and a ventricular pacing pulse in the same cardiac cycle, or a paced AV delay between an Ap event and a ventricular pacing pulse in the same cardiac cycle. The paced AV delay may be programmed to be a slightly longer to allow for atrial pace latency and intra-atrial conduction delay.

In various examples, the electrostimulation circuit 210 may be configured to generate backup pacing pulses for delivery to the heart to excite the myocardium and prevent asystole. The backup pacing pulses may be delivered only if a loss of capture is indicated, characterized by neither the para-Hisian myocardium capture nor the His bundle capture by the delivery of HBP pulses within the capture detection window $W_D$. In another example, the backup pacing pulses may be delivered when the HBP pulses cause para-Hisian myocardium only excitation, without the His bundle excitation. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes.

In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al, U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The timing circuit 239 may time the delivery of the backup pacing, such as HOP at or near the His bundle or in the ventricle, at the end of the capture detection window $W_D$. Alternatively, the timing circuit 239 may time the delivery of a backup pacing at the end of a programmable atrio-ventricular (AV) delay that begins at an As or an Ap event. Upon the expiration of the AV delay, or reaching the end of the capture detection window $W_D$, the timing circuit 239 may initiate a VA timer to detect an As event, or to initiate delivery of an Ap pulse upon the expiration of the VA timer, which marks the beginning of a new cardiac cycle. If the HBD pulse results in His bundle capture or para-Hisian myocardium capture, the timing circuit 239 may initiate the VA timer upon the detection of the far-field ventricular activity (such as the FFR wave) within the capture detection window $W_D$. In an example, an ectopic ventricular beat, such as a PVC, may be sensed in the His bundle region or in the atrium, and trigger the VA timer. Compared to conventional pacing system which triggers the VA timer off the delivery of ventricular pacing (such as RV apex pacing), the VA timer triggered by the sensed FFR wave (in the case of His bundle capture and conducted R-wave) or by the expiration of the capture detection window $W_D$ (in the case of no FFR wave detection) is more suitable for AH pacing mode in which the ventricular pacing is infrequently delivered and may be only reserved as a backup therapy.

The user interface 240 may include an input unit and an output unit. In an example, at least a portion of the user interface 240 may be implemented in the external system 140. The input unit may receive user input such as values of the parameters for physiologic event sensing, and His bundle response and myocardial response detections. The user input may receive user programming of stimulation parameters, or confirmation, rejection, or otherwise modification of the stimulation parameters generated by the parameter adjuster circuit 237. The input unit may include an input device such as a keyboard, on-screen keyboard, mouse, trackball, touchpad, touch-screen, or other pointing or navigating devices. The output unit may include circuitry configured to generate a human-perceptible notification of His bundle response and myocardial response and capture status. The output circuit may be coupled to a display for displaying the received physiologic signals, including tracings of one or more of atrial electrogram, His bundle electrogram, ventricular electrogram, surface electrocardiogram, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media format. In an example, the output unit may generate alerts, alarms, emergency calls, or other forms of warnings to signal the system user about the His bundle capture status. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

Figure 3:
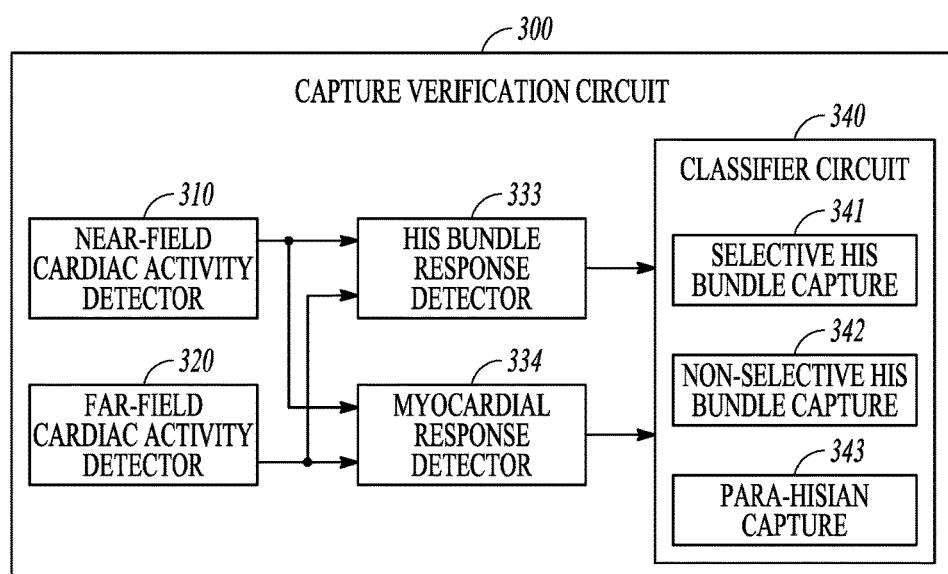
FIG. 3 illustrates generally an example of a capture verification circuit.

FIG. 3 illustrates generally an example of a capture verification circuit 300, which is an embodiment of the capture verification circuit 232. The capture verification circuit 300 includes a near-field cardiac activity detector 310 and a far-field cardiac activity detector 320 coupled to the sensing circuit 220. In an example, the sensing circuit 220 includes a first sensing channel to sense a near-field electrogram (EGM) using a bipolar sense vector comprising two electrodes at or near the His bundle (e.g., the electrodes 112A-B), and a second sensing channel to sense the far-field EGM using a unipolar sense vector comprising a His electrode at or near the His bundle (e.g., one of the electrode 112A or 112B) and a reference electrode (e.g., the housing 116, or one or more electrodes on the housing 116). The first and second sense channels may simultaneously sense the respective EGMs. Alternatively, the sensing circuit 220 includes a sense channel configured to switch between sensing the near-field EGM and sensing the far-field EGM at different time. In an example, the sense channel may be configured to sense the near-field EGM within a first period after the delivery of the HBP pulses, and upon the expiration of the first time period switch to far-field EGM sensing within a second period.

The near-field cardiac activity detector 310 may be configured to detect a near-field para-Hisian myocardial activity from the near-field EGM during a first time window ($W_1$). The myocardial activity is representative of activation of a para-Hisian myocardial tissue in response to the delivery of the HBP pulse. The window $W_1$ may have a programmable duration. In an example, $W_1$ has a duration of approximately 50-70 msec. The far-field cardiac activity detector 320 may be configured to detect a far-field ventricular activity from the far-field EGM during a second time window ($W_2$). The far-field ventricular activity is representative of activation of the His bundle and a ventricle in response to the delivery of the HBP pulse. The window $W_2$ may have a programmable duration. In an example, $W_2$ has a duration of approximately 120 msec. In an example, at least a portion of $W_1$ overlaps with at least a portion of $W_2$. In an example, both $W_1$ and $W_2$ may begin at the delivery of an HBP pulse, or after a short blanking period after the delivery of a HBP pulse. The near-field para-Hisian myocardial activity and the far-field ventricular activity may be detected respectively from the simultaneously sensed near-field EGM and the far-field EGM. In another example, $W_1$ and $W_2$ may be staggered without overlapping to each other. In an example, the first window $W_1$ begins at the delivery of an HBP pulse, or after a short blanking period after the delivery of a HBP pulse, and the second window $W_2$ begins at the end of the first window $W_1$. The near-field para-Hisian myocardial activity may be detected first from the near-field EGM during $W_1$, then far-field ventricular activity may be detected from the far-field EGM during $W_2$ when the sense channel is switched from near-field EGM to far-field EGM sensing.

The capture verification circuit 300 includes a His bundle response detector 333, which is an embodiment of the His bundle response detector 233, and a myocardial response detector 334, which is an embodiment of the myocardial response detector 234. Similar to the capture verification circuit 232 as discussed above with reference to FIG. 2, the His bundle response detector 333 and the myocardial response detector 334 may respectively detect the His bundle response (representative of His bundle capture) and the myocardial response (representative of myocardial capture) using the far-field ventricular activity, such as FFR waves. Additionally or alternatively, the His bundle response detector 333 and the myocardial response detector 334 may respectively detect the His bundle response and the myocardial response using the near-field detection of the para-Hisian myocardial activity. In some examples, the His bundle response detector 333 may detect the His-bundle response using the sensed far-field cardiac electrical signal within $W_2$, and the myocardial response detector 334 may detect the myocardial response using the sensed near-field para-Hisian myocardial activity within $W_1$.

The capture verification circuit 300 includes a classifier circuit 340 configured to classify a tissue response to the delivery of HBP pulses into one of a plurality of capture types. By way of example and not limitation, the capture types may include one or more of a selective His-bundle capture 341, a non-selective His-bundle capture 342, or a para-Hisian capture 343. The selective His-bundle capture 341 refers to excitation (depolarization) of only the His bundle without excitation of the para-Hisian myocardium directly resulting from the HBP pulses. The non-selective His-bundle capture 342 refers to excitation (depolarization) of both the His bundle and para-Hisian myocardium directly resulting from the HBP pulses. The para-Hisian capture 343 refers to excitation (depolarization) of only the para-Hisian myocardium without excitation of the His bundle directly resulting from the HBP pulses. If neither the para-Hisian myocardium nor the His bundle is excited by the HBP pulses, then a loss of capture is indicated.

The classifier circuit 340 may be coupled to the His bundle response detector 333 and the myocardial response detector 334, and classify a tissue response using the detections of the His bundle response and the myocardia response. In an example, the classifier circuit 340 may classify a tissue response to a HBP pulse within a cardiac cycle as a selective His bundle capture if only a His-bundle response is detected and no myocardial response is detected, or a non-selective His bundle capture if both a His-bundle response and a myocardial response are detected, or a para-Hisian capture if only a myocardial response is detected and no His-bundle response is detected.

In some examples, the classifier circuit 340 may classify the tissue capture directly using one or more of the sensed far-field ventricular activity or the near-field para-Hisian myocardial activity, without referring to the His bundle response and the myocardial response. In an example, the classification may be based on the timing of a far-field ventricular activity, such as the HV interval between the delivery of a HBP pulse and a far-field ventricular activity such as a FFR wave. The HV interval for para-Hisian capture may be longer than the HV interval for non-selective His-bundle capture, which may be longer than the HV interval for selective His-bundle capture. The classifier circuit 340 may compare a measured HV interval to different thresholds or value ranges to distinguish various capture types. In another example, the classification may be based on a morphology of the far-field ventricular activity, such as the FFR waves. For example, the selective His-bundle capture may have a narrower FFR wave than the non-selective His-bundle capture and the para-Hisian capture, partly because under the selective His-bundle capture, the HBP pulses directly excite only the His bundle and induce fast conduction through the natural conduction pathways, while under the non-selective His-bundle capture and the para-Hisian capture, the HBP pulses directly excite para-Hisian myocardium and induce slow cell-to-cell conduction. Additionally, the His-bundle capture and para-Hisian capture may have distinct morphological patterns. In an example, differences in morphological pattern may be represented by isoelectric period between the HBP pulse and the detected cardiac response (local myocardial response or far-field ventricular response). For example, selective His-bundle capture may result in an isoelectric period following the HBP pulse, as the depolarization impulse travels peripherally down the specialized conduction system and activates the working myocardium. The activation wave then propagates through working myocardium back up towards the His bundle region. Non-selective capture may result in both His bundle and local working myocardium activation and so there is no isoelectric period as there is an immediate activation of working myocardium, which then fuses with the distal wave that was activated through the specialized conduction system. Para-Hisian pacing may only result in local working myocardium activation. In another example, differences in morphological patterns may also be represented by the polarity of a signal waveform of the sensed cardiac response to the delivery of the HBP pulse. The polarity (positive or negative) may indicate whether the activation wave is going away (negative polarity) or towards (positive polarity) the sense electrodes. For example, selective His-bundle capture may result in the activation wave coming towards the sense electrodes in the His bundle, corresponding to a positive polarity of far-field ventricular response. In contrast, with para-Hisian capture and non-selective His-bundle capture, the activation wave may propagate away from the sense electrodes, corresponding to a negative polarity of the sensed far-field ventricular response. In an example, the classifier circuit 340 may compare the FFR wave width to a threshold (e.g., 120-140 msec) to identify selective His-bundle capture (e.g., falling below the threshold value). The classifier circuit 340 may use a comparison of the FFR wave morphology to a morphology template to distinguish non-selective His-bundle capture from para-Hisian capture. In another example, the classification may be based on both near-field para-Hisian myocardial activity and far-field ventricular activity. Examples of capture verification and classification using the near-field para-Hisian myocardial activity and the far-field ventricular activity are discussed below, such as with reference to FIG. 5.

The stimulation control circuit 236 may use the classification of the capture type to control the delivery of HBP pulses according to one or more stimulation parameters. In an example, if a para-Hisian capture is indicated, the parameter adjuster circuit 237 may adjust one or more stimulation parameters such that the HBP pulses may more likely capture the His-bundle and activate the natural conduction pathways. If a selective or non-selective His-bundle capture is indicated, then no adjustment of the stimulation parameter may be required, because both these capture types can effectively excite the His bundle and produce propagatable action potentials through the natural conduction pathways. However, in some cases, selective His-bundle capture may be preferred over the non-selective His-bundle capture, at least because the non-selective capture may require a higher pacing threshold and consumes more energy than the selective capture, and the direct myocardial excitation and the resultant slow conduction may interfere with the His-bundle capture. In these cases, the parameter adjuster circuit 237 may adjust one or more stimulation parameters to promote selective capture, such that only His-bundle, and no myocardial response, is detected.

Although FIG. 3 illustrates only one near-field cardiac activity detector 310 and only one far-field cardiac activity detector 320 used for capture verification and classification, this is meant only by way of example and not limitation. In various examples, the capture verification circuit 300 may include two or more near-field cardiac activity detectors each coupled to respective electrodes to detect near-field myocardial activity at various locations at or near the His bundle, in the atrium, or other cardiac sites. The electrodes may be on the same lead (e.g., a His bundle lead) or from two or more different leads (e.g., an atrial lead, a His bundle lead, and a ventricular lead). Similarly, the capture verification circuit 300 may include two or more far-field cardiac activity detectors each coupled to respective electrodes to detect far-field cardiac activity from various locations at or near the His bundle, in the atrium, or other cardiac sites. The His bundle response detector 333 and the myocardial response detector 334 may detect respectively the His bundle response (representative of His bundle capture) and the myocardial response (representative of myocardial capture) using far-field ventricular activity detected from multiple different cardiac sites, near-field para-Hisian myocardial activity detected from multiple different cardiac sites, or a combination of the far-field ventricular activity from multiple sites and near-field para-Hisian myocardial activity from multiple sites. Similarly, the classifier circuit 340 may classify the capture status using far-field ventricular activity detected from multiple different cardiac sites, near-field para-Hisian myocardial activity detected from multiple different cardiac sites, or a combination thereof. In an example, the capture verification and/or capture status classification may be based on a near-field para-Hisian myocardial activity with highest signal quality among the multiple near-field para-Hisian myocardial activity from multiple sites, and/or based on a far-field ventricular activity with high signal quality among the multiple far-field ventricular activity from multiple sites.

The detection of His bundle response, the myocardial response, and the capture classification as discussed above may be applied to each of a plurality of cardiac cycles, such that the tissue response to HBP pulse may be assessed on a beat-by-beat basis. In some examples, the capture verification circuit 300 may compute capture statistics using the capture verification and classification results over multiple heart beats, or during a specified time period. Examples of the capture statistics may include percentages, histograms, or other measures of distribution of the selective His-bundle capture, non-selective His-bundle capture, or para-Hisian capture. The capture statistics may indicate HBP efficacy according to the present stimulation parameters. The stimulation control circuit 236 may adjust one or more stimulation parameters based on the capture statistics. For example, if the capture statistics indicate a substantially low percentage of selective His bundle capture (e.g., falling below a first threshold percentage), a substantially high percentage of para-Hisian capture (e.g., exceeding a second threshold percentage), or a substantially high percentage of non-selective His bundle capture (e.g., exceeding a third threshold percentage), then the parameter adjuster circuit 237 may adjust one or more stimulation parameters to promote selective His-bundle capture and more effective cardiac pacing through the natural conduction pathways.

Figure 4:
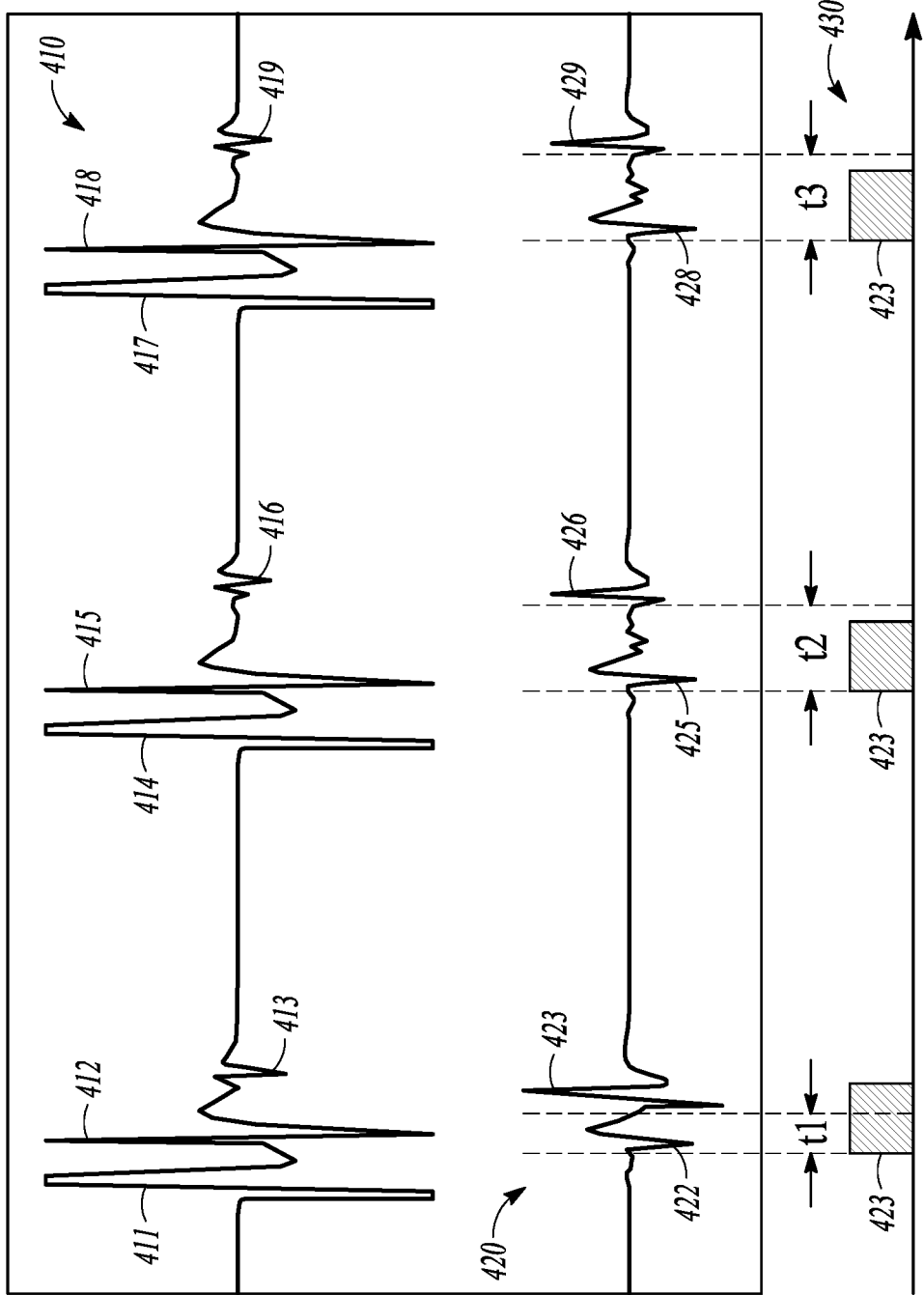
FIG. 4 is a diagram illustrating examples of His-bundle pacing and far-field ventricular responses during His-bundle capture and para-Hisian capture.

FIG. 4 is a diagram illustrating examples of His-bundle pacing and far-field ventricular response during His-bundle capture and para-Hisian capture. Portions of an atrial electrogram (AEGM) 410 and a His bundle electrogram (HEGM) 420 may be sensed and recorded using the His-bundle pacing system 200. The AEGM 410 may be sensed using the sensing circuit 220 via electrodes positioned at an atrium, such as a right atrium of the heart 102. The HEGM 420 may be sensed using the sensing circuit 220 via electrodes positioned at or near a His bundle, such as the electrodes 112A-B positioned at a region distal to the AV node and in the AV septum. The His-bundle pacing system 200 may be programmed to operate in an atrial-Hisian (AH) pacing mode to deliver demand AH pacing pulses. In an example, after delivery of each of atrial pacing pulses 411, 414, and 417, an HBP pulse may be generated by the electrostimulation circuit 210 and is delivered to the target His bundle region upon an expiration of a programmed AH delay, shown as the HBP pulses 422, 425, and 428 in the HEGM 420 corresponding to the atrial pacing pulses 411, 414, and 417. The delivery of the HBP pulses may also be sensed in the AEGM 410, shown as HBP pacing artifacts 412, 415, and 418. In the three cardiac cycles shown in FIG. 4, the HBP pulse 422 directly excites only the His bundle without exciting the para-Hisian myocardium. The His bundle action potential travels through the natural conduction pathways and elicits ventricular depolarization, which is sensed as a far-field ventricular activity such as FFR wave 423. The HBP pulse 425 directly excites only the para-Hisian myocardium without exciting the His bundle, and elicits a slow cell-to-cell propagation of the myocardial action potential propagation via the myocardium, which is sensed as a FFR wave 426. The HBP pulse 428 similarly only directly excites the para-Hisian myocardium, and elicits a FFR wave 429.

The capture verification channel 430 illustrates detecting capture status based on the timing of the far-field ventricular activity in response to the delivery of HBP pulses. The capture verification may be performed using the capture verification circuit 232 or the capture verification circuit 300. An HV interval is computed between the HBP pulses and the resulting FFR wave. In the example illustrated in FIG. 4, the HV interval (t1) between the HBP pulse 422 and the FFR 423 is approximately 40 msec. The HV interval (t2) between the HBP pulse 425 and the FFR 426, and the HV interval (t3) between the HBP pulse 428 and the FFR 429, are approximately 80 msec. The shorter HV interval t1 may be representative of a His bundle capture, and the longer HV intervals t2 and t3 may be representative of para-Hisian myocardial capture without His bundle capture. FIG. 4 illustrates a capture detection window 423 for verifying capture status. The window 423 has a window duration L that may be programmed to be greater than t1 and less than t2 and t3. In an example, L is approximately 50-60 msec. The capture detection window 423 may then be used to distinguish His bundle capture produced by the HBP pulse 422 (t1<L) from para-Hisian capture produced by the HBP pulses 425 and 428 (t2>L and t3>L).

The capture verification may alternatively or additionally be performed using the AEGM 410. In response to delivery of respective HPB pulses 422, 425, and 428, corresponding far-field ventricular activities, such as far-field R waves, may be sensed in the AEGM 410 as 413, 416, and 419. The HV intervals may be measured between the HBP pacing artifact 412 and the FFR 413, between pacing artifact 415 and the FFR 416, and between pacing artifact 418 and the FFR 419. The capture verification circuit 232 may detect His-bundle capture or para-Hisian myocardial capture from the AEGM 410 using the capture detection windows that begin at the HBP pacing artifacts, similar to capture verification from the HEGM 420 using the detection window 423.

Figure 5:
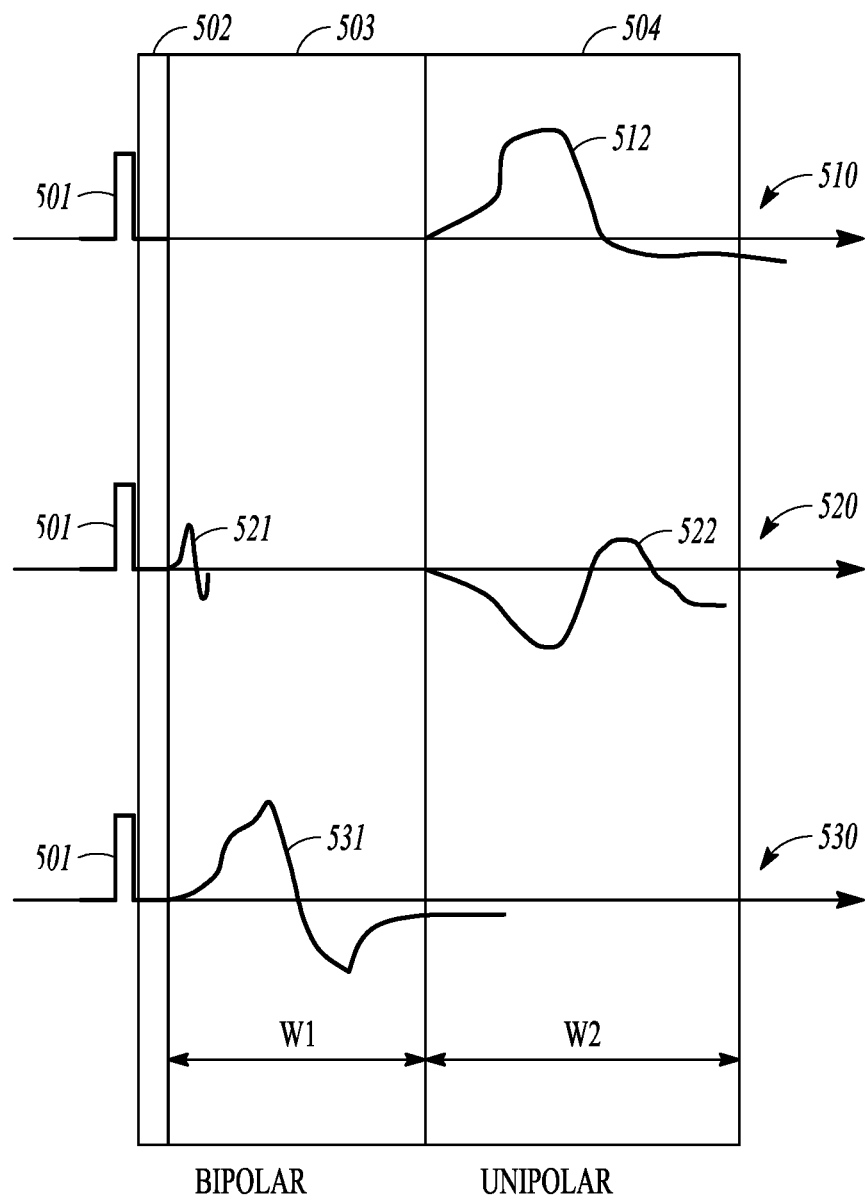
FIG. 5 is a diagram illustrating examples of cardiac events following delivery of a HBP pulse 501 to a His Bundle.

FIG. 5 is a diagram illustrating examples of cardiac events in response to a HBP pulse 501 to a His Bundle, and capture classification based on the cardiac events. The HBP pulse may be generated by the electrostimulation circuit 210, and is delivered to the target His bundle following an AH delay from an intrinsic or paced atrial activation. The HBP pulse may directly excite one or more of the His-bundle tissue or para-Hisian myocardium, resulting in different capture types as previously discussed with reference to FIG. 3. Cardiac events may be detected in two consecutively staggered detection windows $W_1$ and $W_2$. Near-field para-Hisian myocardial activity may be sensed at or near the His-bundle region within the first window $W_1$ using a bi-polar sense vector. Far-field ventricular activity may be sensed at or near the His-bundle region within the second window $W_2$ using a unipolar sense vector. $W_1$ may begin after a blanking period 502 subsequent to the HBP pulse delivery, and has a duration of approximately 50-70 msec. $W_2$ may begin upon the end of $W_1$, and has a duration of approximately 120 msec.

Diagram 510 illustrates tissue response representative of a selective His bundle capture. In response to the HBP pulse 501, no myocardial activity is detected in the first window $W_1$, or a local myocardial activity is elicited by the HBP pulse 501 but has a low intensity (e.g., low amplitude) falling below a detection threshold, such that no detection is declared. A far-field ventricular activity 512 is detected in the second window $W_2$, representing an excitation of the His bundle and a propagation of action potentials through the natural cardiac conduction system. Diagram 520 illustrates tissue response representative of a non-selective His bundle capture. In response to the HBP pulse 501, a myocardial activity 521 is detected in the first window $W_1$. The non-selective His-bundle capture may result in a fusion of at least a portion of slowly propagating action potentials from the local myocardium colliding with the rest of the ventricles that have been excited through the fast natural cardiac conduction system. As a result, the myocardial activity 521 may be a transient event with a short duration. A far-field ventricular activity 522 is detected in the second window $W_2$. The far-field ventricular activity 522 may have similar morphology to the far-field ventricular activity 512 in the case of selective His bundle capture 510, but with some partial slurring or widening. In some examples as illustrated in FIG. 5, the far-field ventricular activity 522 may have a reversed polarity compared to the far-field ventricular activity 512 during selective His bundle capture, due to different propagation direction of the activation relative to the sensing electrodes (e.g., whether the activation moves towards, or away from, the sensing electrodes). Diagram 530 illustrates tissue response representative of a para-Hisian capture. In response to the HBP pulse 501, a myocardial activity 531 is detected sensed in the first window $W_1$. Compared to the transient myocardial activity 521 in non-selective His-bundle capture, the myocardial activity 531 may have a longer duration, at least because the fast natural conduction pathway is activate; and the slowly propagating myocardial action potentials are annihilated by the conduction wave through the fast propagating Purkinje system. As illustrated in 530, no far-field ventricular activity is detected in the second window $W_2$, or a far-field ventricular activity may elicited by the HBP pulse 501 but has a low intensity (e.g., low amplitude) falling below a detection threshold, such that no detection is declared. In some examples, a far-field ventricular activity may be elicited secondary to the slow conduction through myocardium, and thus has a different morphology than the far-field ventricular activity 512 or the far-field ventricular activity 522 where the His bundle capture has been achieved.

In some examples, polarity of unipolar sensed ventricular activity may be used to classify the capture type. For example, a positive unipolar sensed waveform indicates activation coming toward the sensing electrode, and may be representative of selective His bundle capture. Conversely, a negative unipolar sensed waveform indicates activation going away from the sensing electrode, and may be representative of non-selective His bundle capture or para-Hisian capture.

If the tissue response indicates a para-Hisian capture (as illustrated in diagram 530) or a loss of capture (not shown), then backup pacing may be delivered to a target ventricular site or to a His bundle site. The backup pacing may be delivered after expiration of the first and second time windows, such as at the end of the second window $W_2$ as illustrated in FIG. 5. In an example, the backup pacing include high-output pacing pulses with higher pacing energy than conventional pacing pulses.

Figure 6:
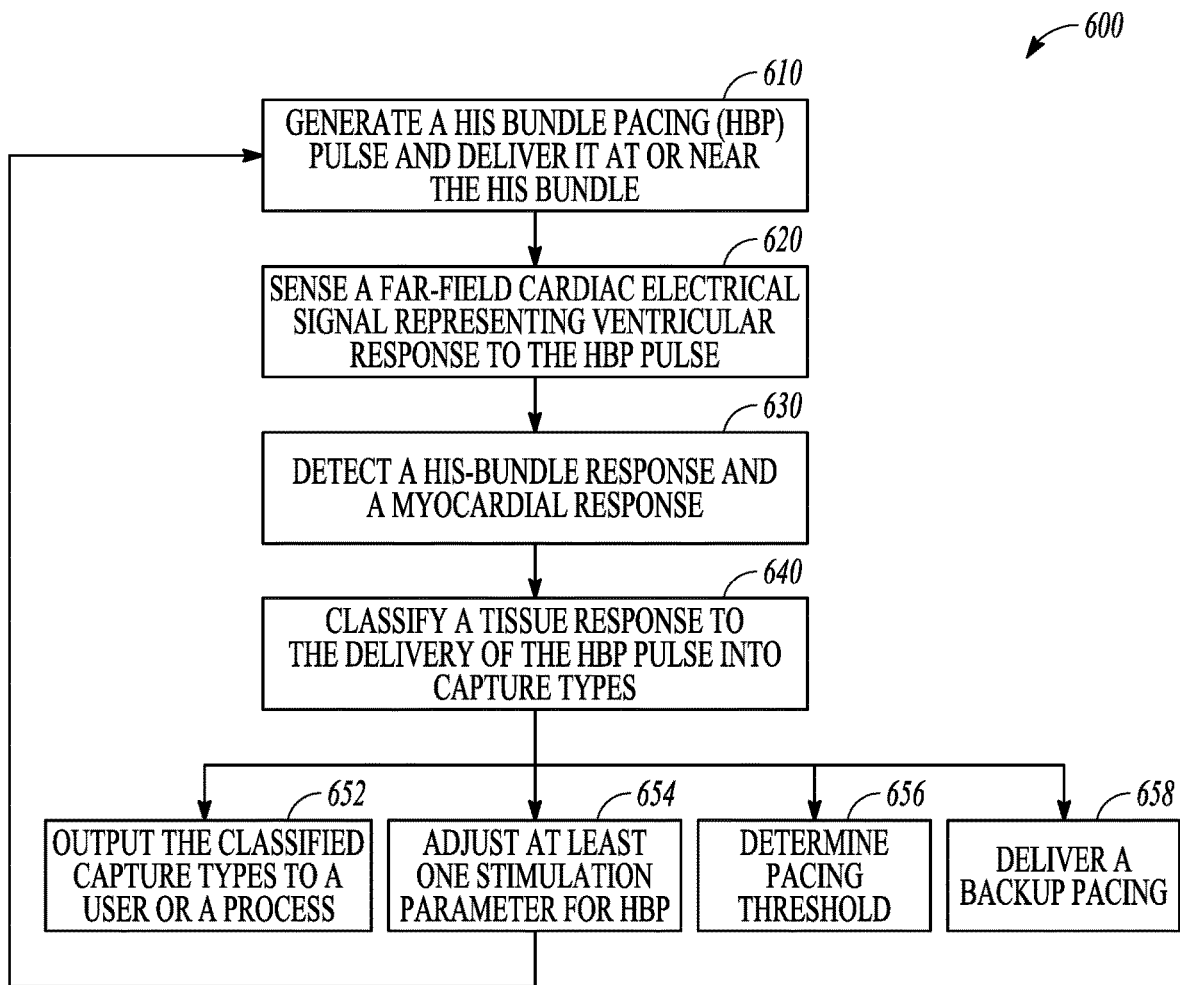
FIG. 6 illustrates generally an example of a method for providing His-bundle pacing to a patient.

FIG. 6 illustrates generally an example of a method 600 for providing His-bundle pacing to a patient using a medical system. The method 600 may be implemented and executed in an ambulatory medical device such as an implantable or wearable medical device, or in a remote patient management system. In an example, the method 600 may be implemented in, and executed by, the IMD 104, one or more devices in the external system 140, or the His-bundle pacing system 200.

The method 600 begins at 610, where a His-bundle pacing (HBP) pulse may be generated and delivered to a target site. The target site may include a region at or near the His bundle 121, such as a region distal to the blocked or slowly conducting AV node and in the AV septum, an interventricular septum region, or a right atrial region near the His-bundle 121. The HBP pulse may be generated by the electrostimulation circuit 210, according to programmed stimulation parameters. Examples of the stimulation parameters may include stimulation site, stimulation mode, stimulation timing, or stimulation strength, among other parameters. The HBP pulses may be delivered via a delivery system including, for example, the lead 106 and one or more of the electrodes 112A-B. In an example, HBP pulses may be delivered in multiple cardiac cycles, such that at least one pulse is delivered within each of the multiple cardiac cycles.

In an example, the HBP pulse may be delivered according to an atrial-Hisian (AH) pacing mode, in which the His-bundle pacing may be delivered in a demand mode following an intrinsic atrial event (As) or an atrial pacing event (Ap). The HBP pulses may be delivered after a latency period from (AH timing) beginning at the As or Ap event. In another example, the HBP pulse may be delivered according to a His-ventricular (HV) pacing mode that involves sequential pacing of the His bundle and the ventricle. The ventricular pacing may be provided in a demand mode, such that the ventricular pacing pulses are delivered only when the His pacing fails to produce propagatable depolarization of the ventricles. In yet another example, the HBP pulse may be delivered according to an AHV pacing mode that involves sequential atrial, Hisian, and ventricular pacing. One or more of the His-bundle pacing or the ventricular pacing may be delivered in a demand mode.

At 620, a far-field cardiac electrical signal representing ventricular response to the HBP pulse may be sensed, such as by using the sensing circuit 220 and one or more electrodes or physiologic sensors disposed at a region at or near the His bundle, or in an atrium. The far-field ventricular response is not directly sensed from the ventricle. Examples of the far-field cardiac electrical signal may include far-field EGMs that contain the information of ventricular depolarization, such as the atrial electrogram (AEGM) 410 or the His bundle electrogram (HEGM) 420 in FIG. 4. In various examples, in addition to the far-field cardiac electrical signal, other physiologic signals indicative of capture pattern of interest in response to the delivery of HBP pulses may be sensed. Examples of such physiologic signals may include an impedance signal, a heart sounds signal, a cardiac pressure signal, among other physiological or hemodynamic signals.

At 630, a His-bundle response and a myocardial response may be detected from the sensed far-field cardiac electrical signal, such as by using the capture verification circuit 232. The His-bundle response is representative of excitation of the His bundle directly resulting from the delivery of the HBP pulse, and the myocardial response is representative of excitation of the myocardium directly resulting from the delivery of the HBP pulse. In an example, the far-field ventricular signal may be sensed in response to HBP pulses delivered to multiple cardiac cycles, such that at least one pulse is delivered in each of the multiple cardiac cycles. A His-bundle response and a respective myocardial response may be detected from each of the multiple cardiac cycles using the far-field cardiac electrical signal sensed within the respective cardiac cycle. The His-bundle response and the myocardial response may each be detected based on timing of the far-field ventricular activity, such as a far-field R (FFR) wave. Additionally or alternatively, the His-bundle response and the myocardial response may each be detected based on a morphology of the far-field ventricular activity, such as a width of the FFR wave. Examples of methods for detecting the His-bundle response and the myocardial response are discussed below, such as with reference to FIGS. 7A-C.

At 640, a tissue response to the delivery of the HBP pulse may be classified into one of a plurality of capture types including, for example, a selective His bundle capture, a non-selective His bundle capture, a para-Hisian capture, or a loss of capture. In an example, the classification may be a beat-by-beat classification of tissue response in each of the multiple cardiac cycles. The classification may be based on detection or non-detection of the His-bundle response, and detection or non-detection of the myocardial response. Examples of classifying the tissue response into one of capture types are discussed below, such as with reference to FIG. 8.

In some examples, the classification of capture types may be based on the sensed far-field ventricular activity and/or the near-field para-Hisian myocardial activity, without referring to the His bundle response or the myocardial response. For example, the capture classification may be based on the time interval (HV interval) between the delivery of a HBP pulse and a far-field ventricular activity, or a morphology of the far-field ventricular activity, such as the FFR wave. In another example, a near-field para-Hisian myocardial activity sensed using a bipolar sense vector and a far-field ventricular activity sensed using a unipolar sense vector may be used together for capture classification, such as discussed above with reference to FIG. 5. In some examples, additional sensor signals, such as cardiac pressure, impedance, heart sounds, or other mechanical or hemodynamic information may be used in capture classification.

The classified capture types may be output to a user (e.g., a clinician) or a process at 652, such as being displayed on a display of the user interface 240. The sensed far-field cardiac electrical signals, the detection results of the His-bundle response and the myocardial response, or the programmed stimulation parameters, among other intermediate measurements or computations, may also be displayed. Additionally or alternatively, the classified capture types may be used to adjust at least one stimulation parameter for HBP at 654, such as via the parameter adjuster circuit 237. The stimulation parameter adjustment may be performed when the tissue response is classified as a para-Hisian response, or as a loss of capture. In some examples, stimulation parameter adjustment may be based on capture statistics computed using the capture verification and classification results over multiple heart beats. Examples of the capture statistics may include percentages, histograms, or other measures of distribution of the selective His-bundle capture, non-selective His-bundle capture, or para-Hisian capture. The stimulation parameter adjustment may be performed when the capture statistics satisfy a specific condition.

The parameter adjustment may include switching to a different stimulation site, using a different pacing vector configurations, adjusting the AH timing with respect to an intrinsic or paced atrial activation, adjusting stimulation strength such as one or more of pulse amplitude, pulse width, pulse frequency, pulse waveform, duty cycle, or stimulation duration. In some examples, the parameter adjustment may include adjusting a stimulation mode, such as switching from AH pacing mode to AHV mode in response to a change in patient condition, such as a development of bundle branch block. The HPB pulses may be generated and delivered at 610, according to the adjusted stimulation parameters to more effectively capture the His bundle, activate the natural conduction pathway, and improve patient cardiac performance.

The classification of the tissue response may additionally or alternatively used to guide a pacing threshold test to determine a proper pacing threshold at 656, such as by using the threshold test circuit 238. The pacing threshold represents minimal energy required to excite the His bundle. In an example, the pacing threshold test may be triggered when the tissue response to HBP pulses is classified as a loss of capture or a para-Hisian capture, in which no His bundle capture is achieved directly by the HBP pulses. Additionally or alternatively, the pacing threshold test may be carried out at the implant of the IMD 104, periodically at specified time period, or upon receiving a user command. The pacing threshold test may include delivering a series of HBP pulses with varying pulse amplitude, such as HBP pulses with decreasing amplitudes in a ramp-down test or HBP pulses with increasing amplitudes in a ramp-up test. Time intervals (HV intervals) between the delivery of HPB pulses and the corresponding sensed far-field ventricular activities (e.g., far-field R waves) may be measured. The pacing threshold may be determined as the pulse amplitude corresponding to a step change in the measured HV intervals, such as a step increase in the measured HV intervals in a ramp-down test. The step change in the HV intervals indicates a transition from a propagatable His-bundle excitation to a local para-Hisian myocardial excitation without His-bundle capture. In some other examples, the pacing threshold test may additionally be based on a change in morphology of the far-field ventricular activations.

At 658, a backup pacing may be delivered when the tissue response to HBP pulses is classified as a loss of capture, or a para-Hisian capture. The backup pacing may be delivered to a target ventricular site via a lead with associated electrodes disposed in or on a ventricle, such as a right ventricle. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses. In addition to backup ventricular pacing, other therapies, such as CRT, BiV pacing, LV-only pacing, single site LV pacing, or multi-site LV pacing may be delivered to improve myocardial contractility and cardiac performance.

Figure 7A:
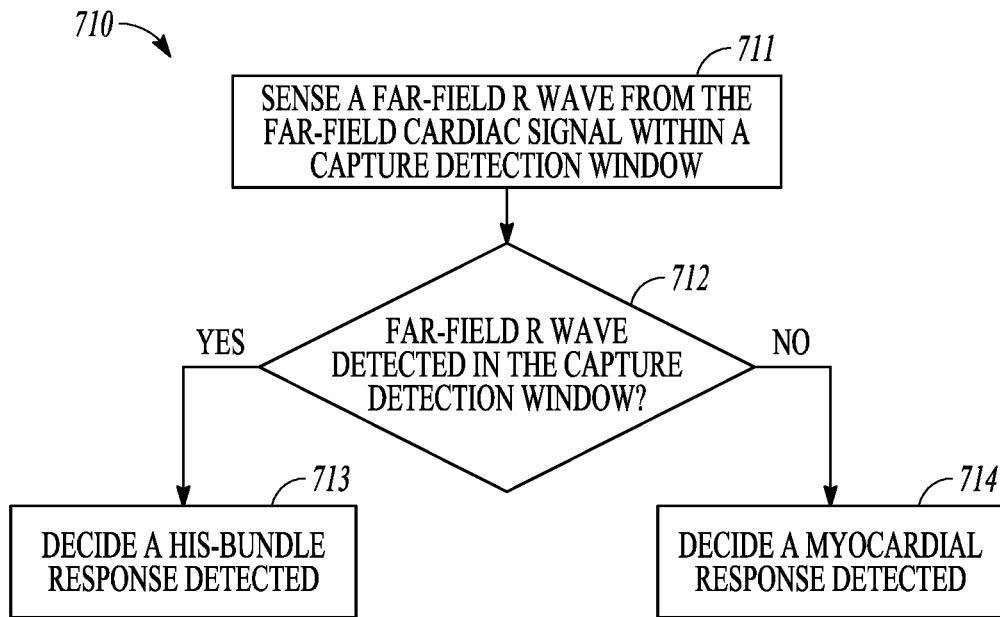
FIGS. 7A-C are flow charts illustrating examples of methods for detecting the His-bundle response and the myocardial response using at least the far-field cardiac electrical signal representative of ventricular activity.
Figure 7B:
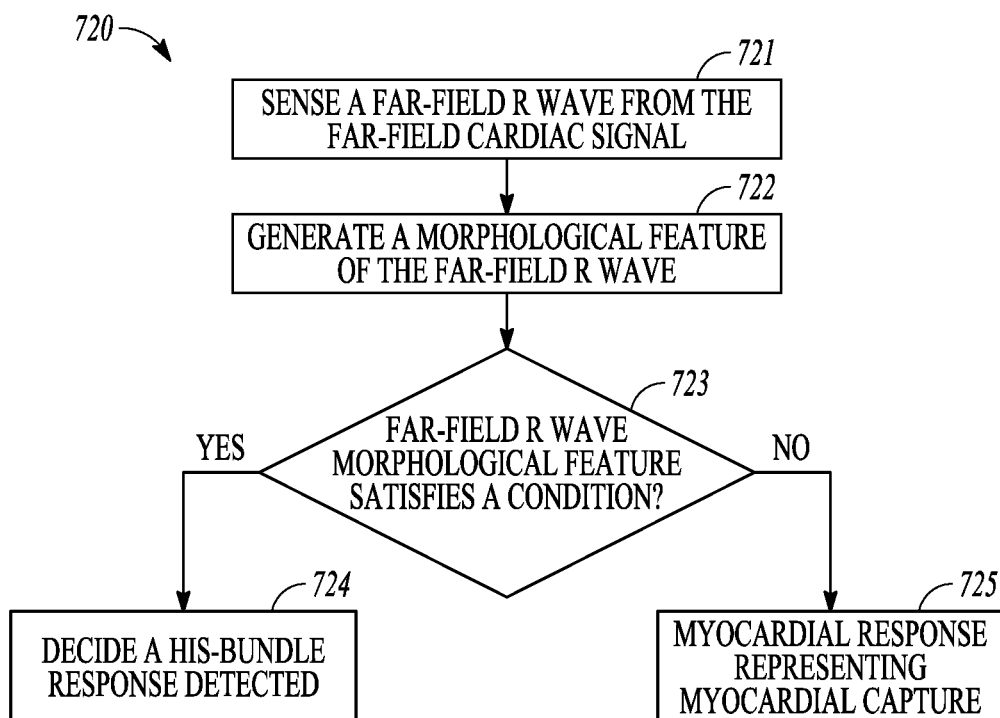
Figure 7C:
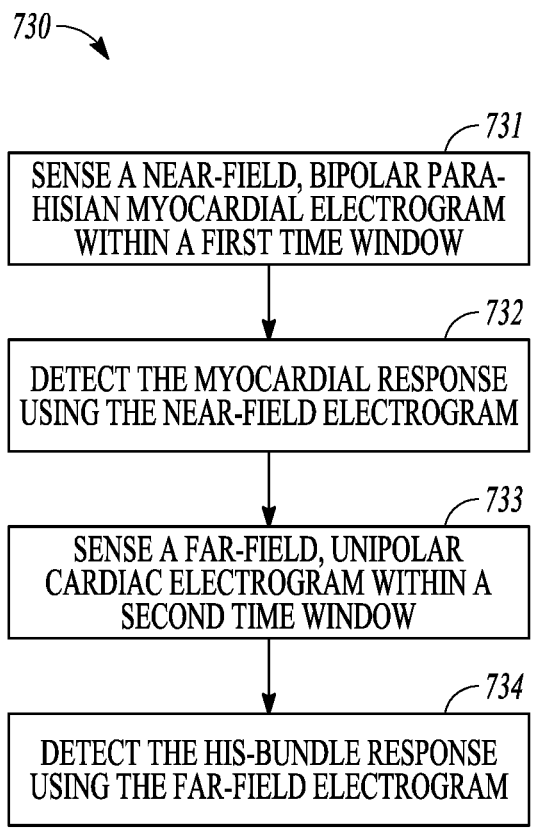

FIGS. 7A-C are flow charts illustrating examples of methods 710, 720, and 730 of detecting His-bundle response and myocardial response using at least the far-field cardiac electrical signal representative of ventricular activity. Each of the methods 710, 720, and 730 is an embodiment of the step 630 of the method 600, and can be implemented in, and executed by, the capture verification circuit 232.

FIG. 7A illustrates a method 710 of detecting the His-bundle response and the myocardial response based on timing of a far-field ventricular response to a HBP pulse. The method 710 begins at 711 to sense a far-field R (FFR) wave from the far-field cardiac signal received at 620. The FFR wave may be sensed within a capture detection window ($W_D$) that begins at the delivery of a HBP pulse, and has a specified window duration (L). In an example, L is approximately 50-120 msec. A His-bundle response may be characterized by a shorter HV interval (measured from the delivery of a HBP pulse to the FFR wave), due to relatively faster conduction of a depolarization wave through the natural conduction pathways. A myocardial response may be characterized by a longer HV interval because of relatively slower, cell-to-cell conduction of the depolarization wave through the myocardium.

The window $W_D$ may distinguish slower myocardial response from faster His-bundle response. If at 712 a FFR is detected within the window $W_D$, then a His-bundle response is deemed detected at 713. The detection of the His-bundle response indicates an excitation of the His bundle directly resulting from the delivery of the HBP pulses. If at 712 no FFR is detected within the window $W_D$, then the FFR is likely outside $W_D$, indicating a slow conduction through the myocardium. Accordingly, a myocardial response is deemed detected at 714. The detection of the myocardial response indicates an excitation of the para-Hisian myocardium directly resulting from the delivery of the HBP pulses. The detected His-bundle response and the myocardial response may be used to classify tissue response into a capture type, or to titrate therapy delivery such as by adjusting one or more stimulation parameters.

FIG. 7B illustrates a method 720 of detecting the His-bundle response and the myocardial response based on a morphology of far-field ventricular response to delivery of a HBP pulse. The method 720 begins at 721 to sense a FFR wave from the far-field cardiac signal received at 620.

Unlike the method 710, which detects the FFR wave within the window $W_D$, the FFR wave detection at 721 is not limited within a particular time duration. At 722, a morphological feature of the sensed FFR may be extracted. Due to their different conduction pathways and conduction properties (e.g., velocity), the His-bundle response and the myocardial response may demonstrate different ventricular EGM morphologies. An example of the morphological feature is a width of the sensed FFR wave. A His-bundle response may be characterized by a narrower FFR wave or far-field QRS complex due to relatively faster conduction through the natural conduction pathways. A myocardial response may be characterized by a wider FFR wave or far-field QRS complex because of relatively slower, cell-to-cell conduction through the myocardium. Other examples of the morphological features may include a slope of the upstroke or down-stroke branch of the R wave, or an area under the curve of the FFR wave, among others.

At 723, the morphological feature of the FFR wave may be compared against a condition, such as a threshold, a range, or a morphology template. In an example, if the measured width the FFR wave satisfies a specified condition such as falling below a width threshold, then a His-bundle response is deemed detected at 724. If the measured width of the FFR wave fails to satisfy the specified condition such as exceeding a width threshold, then a myocardial response is deemed detected at 725. In an example, the width threshold is approximately 90-120 msec. In another example, the width threshold is approximately 120-140 msec. The detected His-bundle response and the myocardial response may be used to classify tissue response into a capture type, or to titrate therapy delivery such as by adjusting one or more stimulation parameters.

FIG. 7C illustrates a method 730 of detecting the His-bundle response and the myocardial response based on based on a near-field para-Hisian myocardial EGM and a far-field cardiac EGM sensed at or near the His bundle or in an atrium. The method 730 begins at 731 to sense a near-field para-Hisian myocardial EGM within a first time window $W_1$, such as using a bipolar sense vector comprising two electrodes at or near the His bundle. In an example, $W_1$ has a duration of 50-70 msec. At 732, a myocardial response may be detected from the near-field para-Hisian myocardial EGM within the window $W_1$. In the example illustrated in FIG. 5, the myocardial activity 521 and the myocardial activity 531 are sensed within the first window $W_1$ using a hi-polar sense vector, and are representative of capture of the near-field para-Hisian myocardium directly by the HBP pulse.

At 733, a far-field cardiac EGM may be sensed within a second time window $W_2$, such as using a unipolar sense vector comprising an electrode at or near the His bundle and a reference electrode, such as the housing 116 of the IMD 104. In an example, $W_2$ has a duration of 120 msec. At 734, a His-bundle response may be detected using the far-field cardiac EGM within the window $W_2$. In an example, at least a portion of $W_1$ overlaps with the $W_2$. Alternatively, $W_1$ and $W_2$ may be staggered without overlapping. In the example as illustrated in FIG. 5, the ventricular activation 512 and the ventricular activation 522 are sensed within the second window $W_2$ using a unipolar sense vector, and are representative of excitation of the His bundle directly by the HBP pulse. The detected His-bundle response and the myocardial response may be used to classify tissue response into a capture type, or to titrate therapy delivery such as by adjusting one or more stimulation parameters.

Figure 8:
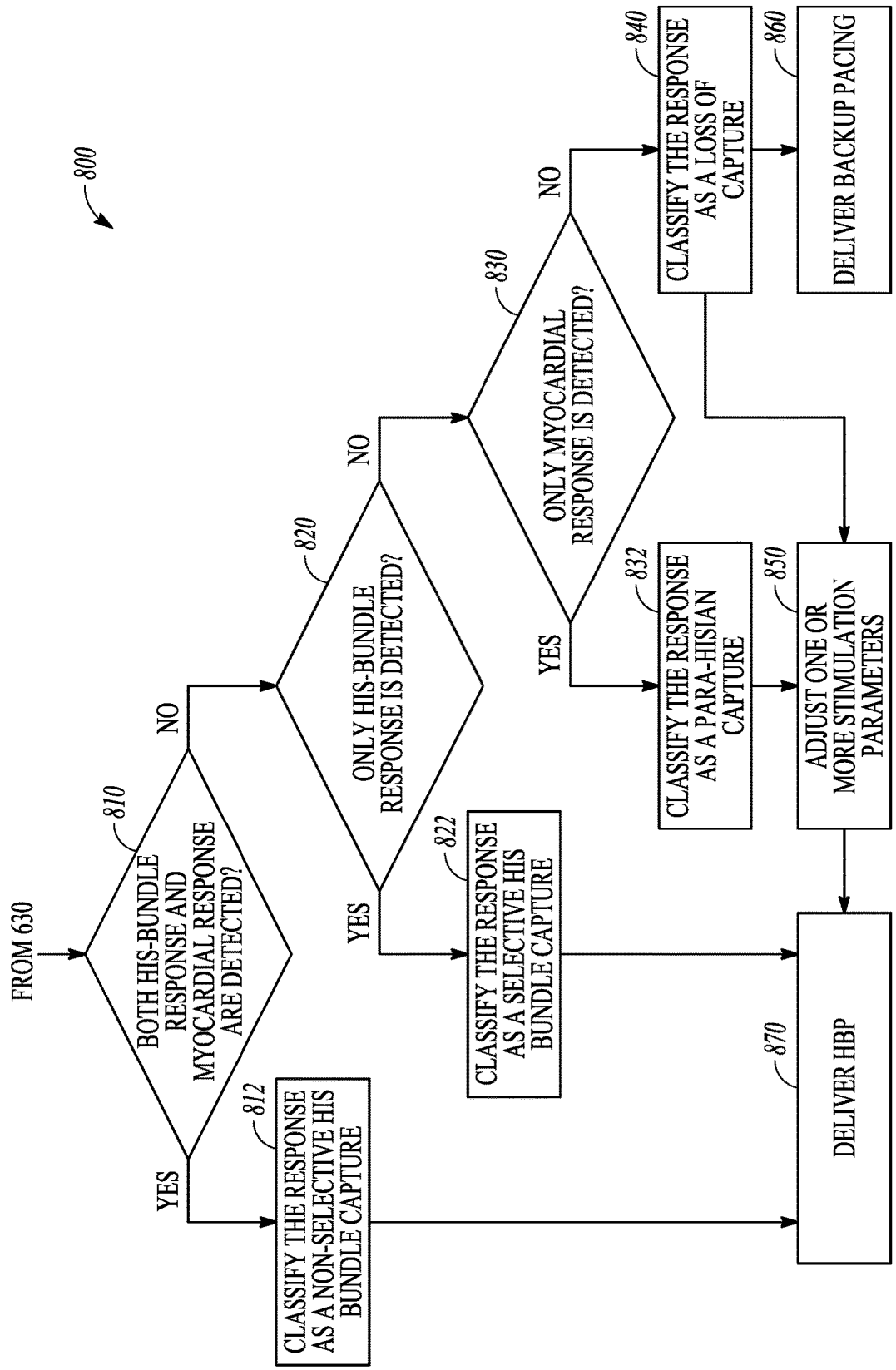
FIG. 8 is a flow chart illustrating an example of a method for classifying a tissue response to HBP pulses into one of a plurality of capture types, and delivering electrostimulation in accordance with the classification result.

FIG. 8 is a flow chart illustrating an example of a method 800 for classifying a tissue response to HBP pulses into one of a plurality of capture types, and delivering electrostimulation in accordance with the classification result. By way of example and not limitation, the capture types may include a selective His-bundle capture, a non-selective His-bundle capture, a para-Hisian capture, or a loss of capture. The capture classification in the method 800 is an embodiment of the step 640 of the method 600, and can be implemented in, and executed by, the classifier circuit 340.

The method 800 may classify the tissue response based on the detected His-bundle response and the detected myocardial response obtained at step 630. If at 810 both the His-bundle response and the myocardial response are detected, indicating excitation of both the His bundle and the para-Hisian myocardium directly resulting from the HBP pulse, then at 812 the tissue response may be classified as a non-selective His bundle capture. Otherwise, if only the His-bundle response is detected without myocardial response detection at 820, indicating excitation of only the His bundle directly resulting from the HBP pulse without excitation of para-Hisian myocardium, then at 822 the tissue response may be classified as a selective His bundle capture. If only the myocardial response is detected without His-bundle response detection at 830, indicating excitation of only the para-Hisian myocardium directly resulting from the HBP pulse without His bundle excitation, then at 832 the tissue response may be classified as a para-Hisian capture. If neither the His-bundle response nor the myocardial response is detected, indicating a failure of the HBP pulse to excite the His bundle and the para-Hisian myocardium, then the tissue response may be classified as loss of capture at 840.

The capture type classification at 812, 822, 832 and 840 may be used to control the delivery of HBP pulses according to one or more stimulation parameters. Because the selective His-bundle capture at 812 and the non-selective His-bundle capture at 822 both effectively excite the His bundle and produce prorogation of action potentials through the natural conduction pathways, no adjustment of the stimulation parameter is required; and the ongoing HBP therapy may be continued at 870. In some examples, the parameter adjustment may be performed to promote selective capture if the non-selective His-bundle capture is indicated at 822. That is, the step 822 is optionally followed by step 850 to adjust one or more stimulation parameters.

If a para-Hisian capture is indicated at 832, one or more stimulation parameters may be adjusted at 850. At 870, the HBP therapy may be delivered according to the adjusted stimulation parameters to capture the His-bundle and elicit ventricular depolarization through the natural conduction pathways. The parameter adjustment may be continued until the His-bundle response is detected, which indicates that HBP pulses elicit propagatable excitation of the His bundle. In some examples, the parameter adjustment may be continued until only the His-bundle response, but no myocardial response, is detected, which indicates that HBP pulses elicit only propagatable excitation of the His bundle without excitation of the para-Hisian myocardium.

If a loss of capture is indicated at 840, then backup pacing may be delivered at 860 to excite the myocardium and evoke cardiac contraction. The loss of capture at 840 may additionally or alternatively trigger an adjustment of one or more stimulation parameters at 850. The backup pacing may include high-output pacing (HOP) pulses, which have higher pacing energy than conventional pacing pulses. The backup pacing may be delivered to a target ventricular site in a right ventricle, such as the RV apex, or delivered to the His bundle site for delivering the HBP pulses. In some examples, the backup pacing may also be delivered if a para-Hisian capture is indicated at 832. That is, the step 832 is optionally followed by step 860 to deliver backup ventricular pacing.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a heart, comprising:
   an electrostimulation circuit configured to generate a His-bundle pacing (HBP) pulse for delivery at or near a His bundle of the heart according to one or more pacing parameters;
   a sensing circuit configured to sense, in response to the delivery of the HBP pulse at or near the His bundle, a near-field para-Hisian electrical signal and a far-field cardiac electrical signal;
   a capture verification circuit configured to:
      detect, from the sensed far-field cardiac electrical signal, a His-bundle response representative of excitation of the His bundle directly resulting from the delivery of the HBP pulse; and
      detect, from the sensed near-field para-Hisian electrical signal, a para-Hisian myocardial response representative of excitation of a para-Hisian myocardial tissue of the heart directly resulting from the delivery of the HBP pulse; and
   a control circuit configured to adjust at least one of the one or more pacing parameters based on the detected His-bundle response and the detected para-Hisian myocardial response.

2. The system of claim 1, wherein
   the electrostimulation circuit, coupled to the parameter adjuster circuit, is configured to generate the HBP pulse for delivery at or near the His bundle according to the adjusted at least one pacing parameter to excite the His bundle.

3. The system of claim 1, comprising a timing circuit configured to time the delivery of the HBP pulse after an atrial-to-His bundle (AH) interval from an intrinsic atrial activation or an atrial pacing event.

4. The system of claim 1, wherein the sensing circuit is configured to detect a far-field R wave from the far-field cardiac electrical signal, and the capture verification circuit is configured to detect the His-bundle response and the para-Hisian myocardial response based on a timing of the detected far-field R wave relative to the delivery of the HBP pulse.

5. The system of claim 4, wherein the capture verification circuit is configured to detect the His-bundle response if the far-field R wave is detected within a capture detection window, and to detect the para-Hisian myocardial response if no far-field R wave is detected within the capture detection window.

6. The system of claim 5, wherein the control circuit is configured to time a delivery of an atrial pacing pulse after a ventriculoatrial interval, the ventriculoatrial interval beginning at the detected far-field R wave within the capture detection window, or at the end of the capture detection window if no far-field R wave is detected within the capture detection window.

7. The system of claim 5, wherein the electrostimulation circuit is configured to deliver backup pacing at an end of the capture detection window if the capture verification circuit fails to detect the His-bundle response directly resulting from the delivery of the HBP pulse.

8. The system of claim 7, wherein the backup pacing includes a high-output pacing.

9. The system of claim 7, wherein the electrostimulation circuit is electrically coupled to one or more electrodes disposed at or near the His bundle or in the ventricle to deliver the backup pacing.

10. The system of claim 1, wherein the sensing circuit is configured to detect a far-field R wave from the far-field cardiac electrical signal, and the capture verification circuit is configured to detect the His-bundle response if a width of the far-field R wave falls below a width threshold, and to detect the para-Hisian myocardial response if the width of the far-field R wave exceeds the width threshold.

11. The system of claim 1, wherein the control circuit is configured to determine a pacing threshold representing minimal energy to directly excite the His bundle, wherein:
   the electrostimulation circuit is configured to deliver HBP pulses at or near the His bundle according to a pacing parameter taking a plurality of values;
   the sensing circuit is configured to sense respective far-field R waves in response to the delivery of HBP pulses; and
   the control circuit is configured to determine the pacing threshold based on a step change in time intervals between the delivery of HBP pulses and the respective far-field R waves.

12. The system of claim 11, wherein the electrostimulation circuit is configured to deliver a series of HBP pulses with decreasing pacing amplitude, and the control circuit is configured to determine the pacing threshold to be a pacing amplitude corresponding to a step increase in the measured time intervals between the delivery of HBP pulses and the respective far-field R waves.

13. A method for operating a pacing system to stimulate a heart, the method comprising:
   generating a His-bundle pacing (HBP) pulse using an electrostimulation circuit and delivering the HBP pulse at or near the His bundle according to one or more pacing parameters;
   in response to the delivery of the HBP pulse at or near the His bundle, sensing a near-field para-Hisian electrical signal and a far-field cardiac electrical signal using a sensing circuit;
   detecting a His-bundle response from the sensed far-field cardiac electrical signal using a capture verification circuit, the His-bundle response representative of excitation of the His bundle directly resulting from the delivery of the HBP pulse;

detecting a para-Hisian myocardial response from the sensed near-field para-Hisian electrical signal using the capture verification circuit, the para-Hisian myocardial response representative of excitation of the myocardial tissue directly resulting from the delivery of the HBP pulse; and adjusting at least one of the one or more pacing parameters using a control circuit based on the detected His-bundle response and the detected para-Hisian myocardial response.

14. The method of claim 13, wherein adjusting the at least one of the one or more pacing parameters is performed in response to no detection of the His-bundle response directly resulting from the delivery of the HBP pulse.

15. The method of claim 13, wherein delivering the HBP pulse includes timing the delivery of the HBP pulse after an atrial-to-His bundle (AH) interval from an intrinsic atrial activation or an atrial pacing event.

16. The method of claim 13, comprising detecting a far-field R wave from the sensed far-field cardiac electrical signal, and detecting the His-bundle response and the para-Hisian myocardial response based on a timing of the detected far-field R wave relative to the delivery of the HBP pulse.

17. The method of claim 16, comprising detecting the His-bundle response if the far-field R wave is detected within a capture detection window, and detecting the para-Hisian myocardial response if no far-field R wave is detected within the capture detection window.

18. The method of claim 17, comprising delivering backup pacing at an end of the capture detection window if no His-bundle response is detected with the capture detection window.

19. The method of claim 13, comprising detecting a far-field R wave from the sensed far-field cardiac electrical signal, and detecting the His-bundle response and the para-Hisian myocardial response based on a width of the detected far-field R wave of the detected far-field R wave.

20. The method of claim 13, comprising determining a pacing threshold representing minimal energy to directly excite the His bundle, the determination of the pacing threshold including:

delivering a series of HBP pulses with decreasing pacing amplitude at or near the His bundle over multiple cardiac cycles;

sensing, from each of the multiple cardiac cycles, a respective far-field R wave in response to the delivery of HBP pulse; and determining the pacing threshold based on a step increase in time intervals between the delivery of HBP pulses and the respective far-field R waves.

* * * * *